United States Patent
Jensen et al.

(12) 
(10) Patent No.: US 6,407,241 B1
(45) Date of Patent: Jun. 18, 2002

(54) PROCESS AND INTERMEDIATES FOR THE PREPARATION OF IMIDAZOLIDINONE αV INTEGRIN ANTAGONISTS

(75) Inventors: Mark S Jensen, Holmdel; Michael Palucki, Belle Mead; Nelo R. Rivera, Scotch Plains; Kenneth M. Wells, Neshanic Station; Yi Xiao, Fanwood; Yaling Wang, Westfield; Chunhua Yang, Edison; Nobuyoshi Yasuda, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/707,403

(22) Filed: Nov. 7, 2000

Related U.S. Application Data
(60) Provisional application No. 60/163,979, filed on Nov. 8, 1999.

(51) Int. Cl.[7] ................ C07D 471/04; C07D 213/64
(52) U.S. Cl. ................ 546/122; 546/300; 546/301; 544/238; 544/264; 544/333; 544/405
(58) Field of Search ................ 546/122, 300, 546/301; 544/405, 333, 264, 238

(56) References Cited

U.S. PATENT DOCUMENTS
| | | |
|---|---|---|
| 5,952,341 A | 9/1999 | Duggan et al. |
| 6,017,926 A | 1/2000 | Askew et al. |
| 6,048,861 A | 4/2000 | Askew |

FOREIGN PATENT DOCUMENTS
| | | |
|---|---|---|
| WO | WO 98/18460 | 5/1998 |
| WO | WO 99/31061 | 6/1999 |
| WO | WO 99/31099 | 6/1999 |

*Primary Examiner*—Evelyn Mei Huang
(74) *Attorney, Agent, or Firm*—Philippe L. Durette; Melvin Winokur

(57) ABSTRACT

A novel process is provided for the preparation of imidazolidinone αvβ3/αvβ5 integrin antagonists, and the useful intermediates obtained therein. These compounds are antagonists of αvβ3/αvβ5 integrin receptors and thus useful for inhibiting bone resorption and treating and preventing osteoporosis. Also disclosed is 3-{2-oxo-3-[3-(5,6,7,8-tetrahydro-[1,8]naphthyridin-2-yl)-propyl]imidazolidin-1-yl}-3(S)-(6-methoxy-pyridin-3-yl)-propionic acid in the form of a hemihydrate.

13 Claims, No Drawings

PROCESS AND INTERMEDIATES FOR THE PREPARATION OF IMIDAZOLIDINONE αV INTEGRIN ANTAGONISTS

CROSS-REFERENCE TO RELATED APPLICATIONS

The present application claims priority of U.S. provisional application Serial No. 60/163,979, filed Nov. 8, 1999, the content of which is hereby incorporated by reference.

BACKGROUND OF THE INVENTION

The present invention provides an improved process for the preparation of imidazolidinone αvβ3/αvβ5 integrin antagonists of general structural formula (I).

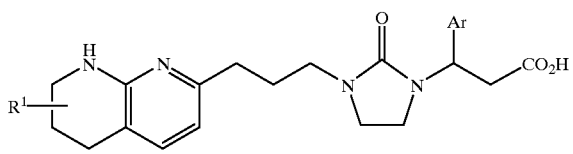

(I)

The present invention also provides intermediates useful in the disclosed process.

The compounds of structural formula (I), along with their use as αvβ3/αvβ5 integrin antagonists for inhibiting bone resorption and treating and/or preventing osteoporosis, were disclosed in U.S. Pat. No. 6,017,926 (Jan. 25, 2000), which is incorporated by reference herein in its entirety, and in WO 99/31099 (published Jun. 24, 1999). The compounds disclosed therein are also useful in inhibiting vascular restenosis, diabetic retinopathy, macular degeneration, angiogenesis, atherosclerosis, inflammatory arthritis, cancer, and metastatic tumor growth.

U.S. Pat. No. 6,017,926 also described a process for preparing the compounds of formula (I). However, a large number of synthetic transformations was required (the longest linear sequence being about 14 steps) with an overall yield of less than 5%. Silica gel column chromatography was required after most of the steps, and final products were obtained with an enantiomeric purity of less than 90%.

With the present invention there are produced more efficiently compounds of structural formula (I) with an enantiomeric purity in excess of 99% in considerably fewer chemical steps (the longest linear sequence being 10 steps) with an overall yield of about 30%. Moreover, a smaller number of chromatographic purification steps is necessary throughout the synthetic sequence.

SUMMARY OF THE INVENTION

This invention is concerned with a process for preparing compounds of structural formula (I) and certain useful intermediates obtained during that process.

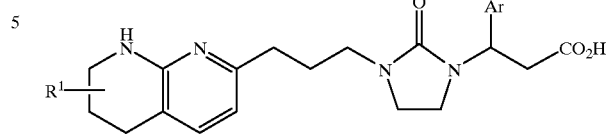

(I)

The novel process and novel intermediates can be exemplified in the following embodiment, which illustrates the preparation of 3-{2-oxo-3-[3-(5,6,7,8-tetrahydro-[1,8]naphthyridin-2-yl)-propyl]imidazolidin-1-yl}-3(S)-(6-methoxypyridin-3-yl)-propionic acid (3-4). The overall process converges two Series A and B of reaction steps, each producing a key intermediate, into a third Series C of steps in which the two intermediates are combined to ultimately produce the desired products of structural formula (I). Series A affords intermediates exemplified by 2-6, and Series B yields intermediates exemplified by 1-8.

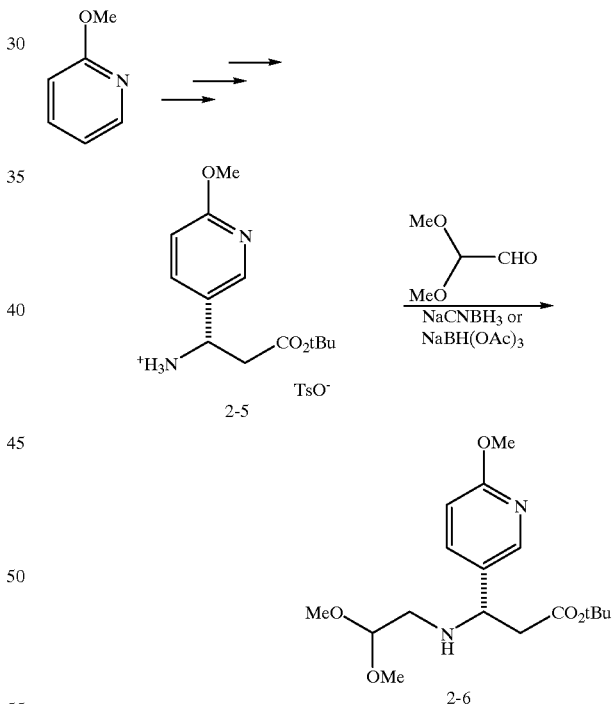

-continued

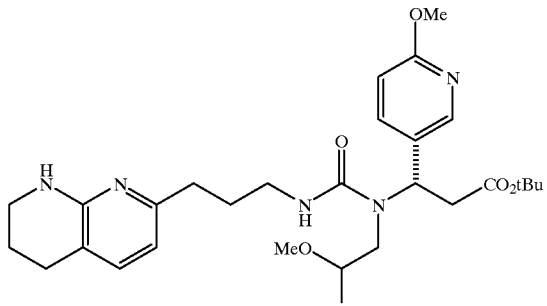

3-1

↓ H₂SO₄

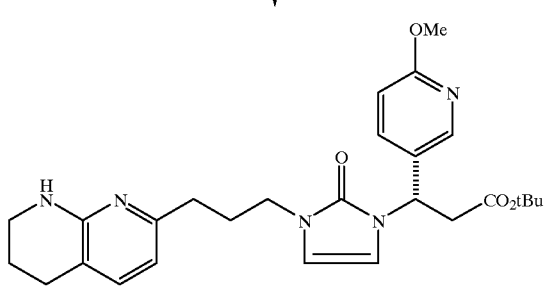

3-2

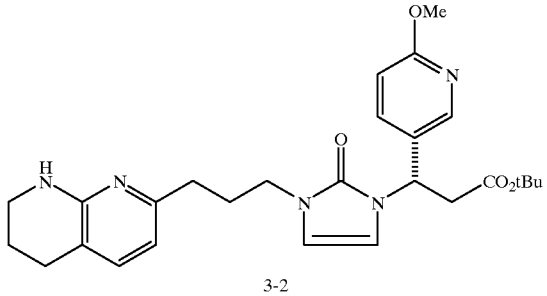

3-2

| 1. acid  or  1. H₂
| 2. H₂        2. acid

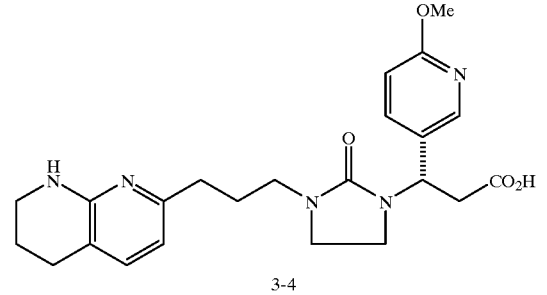

3-4

Also provided are intermediate compounds which are useful for the preparation of compounds of structural formula (I).

Another aspect of the present invention provides compound 3-4 in the form of a hemihydrate as well as a method for the preparation of the hemihydrate.

The products of the present process are antagonists of αvβ3/αvβ5 integrin receptors and therefore useful for inhibiting bone resorption and treating and/or preventing osteoporosis. They are also useful in inhibiting vascular restenosis, diabetic retinopathy, macular degeneration, angiogenesis, atherosclerosis, inflammnatory arthritis, cancer, and metastatic tumor growth.

DETAILED DESCRIPTION OF THE INVENTION

The present invention provides an efficient process for the preparation of compounds of structural formula (I):

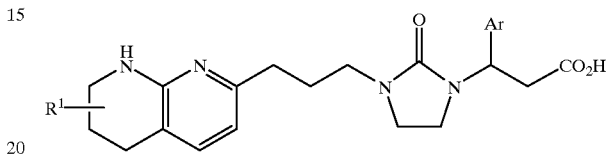

wherein

Ar is mono- or di-substituted phenyl, naphthyl, pyridyl, furyl, thienyl, pyrrolyl, oxazolyl, thiazolyl, isoxazolyl, isothiazolyl, imidazolyl, tetrazolyl, pyrazolyl, pyrimidyl, pyrazinyl, quinolyl, isoquinolyl, benzofuryl, benzothienyl, benzimidazolyl, benzthiazolyl, benzoxazolyl, indolyl, isoindolyl, purinyl, or carbazolyl, wherein the substituent is independently selected from the group consisting of hydrogen, $C_{1-6}$ alkyl, halogen, $C_{3-6}$ cycloalkyl, $C_{1-3}$ acylamino, $C_{1-4}$ alkoxy, $C_{1-5}$ alkoxycarbonyl, cyano, trifluoromethyl, trifluoromethoxy, hydroxy, amino, $C_{1-4}$ alkylamino, di-$C_{1-4}$ alkylamino, and $C_{1-5}$ alkylcarbonyloxy; and $R^1$ is selected from the group consisting of hydrogen, halogen, $C_{1-10}$ alkyl, $C_{3-6}$ cycloalkyl, and $C_{1-3}$ alkoxy;

which comprises the steps of:

(a) producing a compound of structural formula (III):

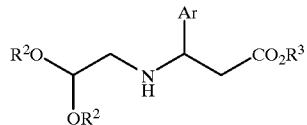

wherein $R^2$ is $C_{1-4}$ alkyl and $R^3$ is $C_{1-4}$ alkyl, phenyl-$C_{1-3}$ alkyl, diphenylmethyl, or triphenylmethyl;

by treating a compound of structural formula (V):

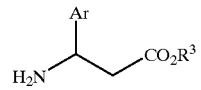

with glyoxal-1,1-di-$C_{1-4}$ alkyl acetal in the presence of a reducing agent and isolating the resulting product;

(b) preparing a compound of structural formula (II):

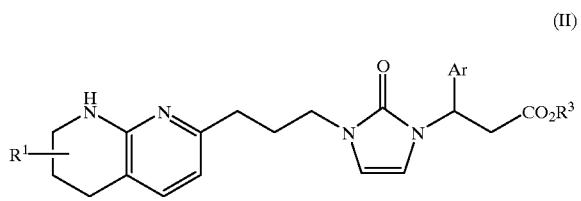

(II)

by treating an amine of structural formula (III):

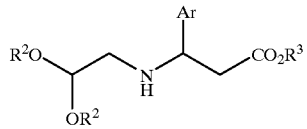

(III)

wherein $R^2$ is $C_{1-4}$ alkyl and $R^3$ is $C_{1-4}$ alkyl, phenyl-$C_{1-3}$ alkyl, diphenylmethyl, or triphenylmethyl;
with an amine of structural formula (IV),

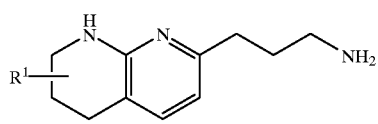

(IV)

wherein $R^1$ is as defined above, in the presence of phosgene or a phosgene equivalent and base to produce a compound of structural formula (VI):

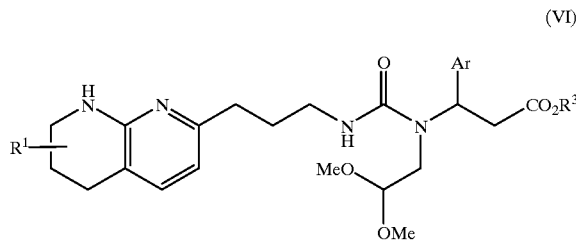

(VI)

followed by treatment with aqueous acid;
(c) cleaving the $R^3$ protecting group in a compound of structural formula (II) to afford a compound of structural formula (VII),

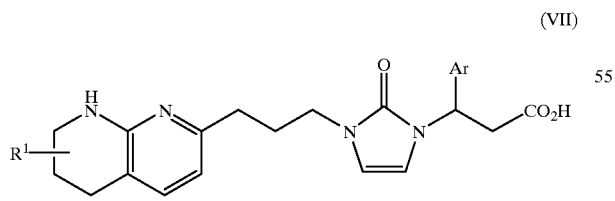

(VII)

(d) reducing the imidazolin-2-one double bond in a compound of structural formula (VII), and
(e) isolating the resulting product.

The order in which the last two steps of the process of the present invention are carried out may be reversed such that the imidazolin-2-one double bond in a compound of structural formula (II):

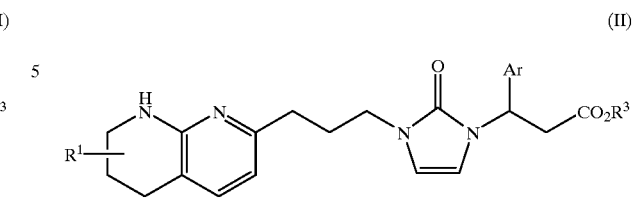

(II)

is first reduced to afford a compound of structural formula (VIII):

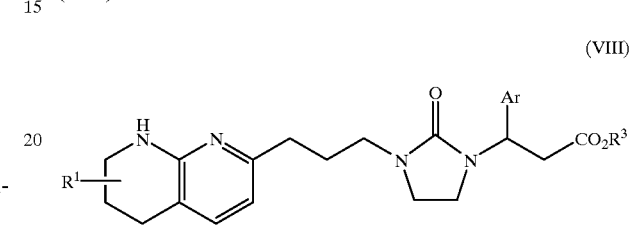

(VIII)

and the $R^3$ protecting group in a compound of structural formula (VIII) is then cleaved to afford a compound of structural formula (I).

In one embodiment of the present invention, there is provided a process for preparing a compound of structural formula (I):

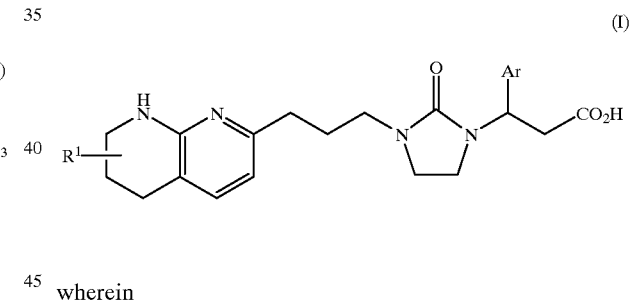

(I)

wherein

Ar is mono-or di-substituted phenyl, naphthyl, pyridyl, furyl, thienyl, pyrrolyl, oxazolyl, thiazolyl, isoxazolyl, isothiazolyl, imidazolyl, tetrazolyl, pyrazolyl, pyrimidyl, pyrazinyl, quinolyl, isoquinolyl, benzofuryl, benzothienyl, benzimidazolyl, benzthiazolyl, benzoxazolyl, indolyl, isoindolyl, purinyl, or carbazolyl, wherein the substituent is independently selected from the group consisting of hydrogen, $C_{1-6}$ alkyl, halogen, $C_{3-6}$ cycloalkyl, $C_{1-3}$ acylamino, $C_{1-4}$ alkoxy, $C_{1-5}$ alkoxycarbonyl, cyano, trifluoromethyl, hydroxy, trifluoromethoxy, amino, $C_{1-4}$ alkylamino, di-$C_{1-4}$ alkylamnino, and $C_{1-5}$ alkylcarbonyloxy; and $R^1$ is selected from the group consisting of hydrogen, halogen, $C_{1-10}$ alkyl, $C_{3-6}$ cycloalkyl, and $C_{1-3}$ alkoxy;

which comprises the steps of:

(a) cleaving the $R^3$ protecting group in a compound of structural formula (II):

(II)

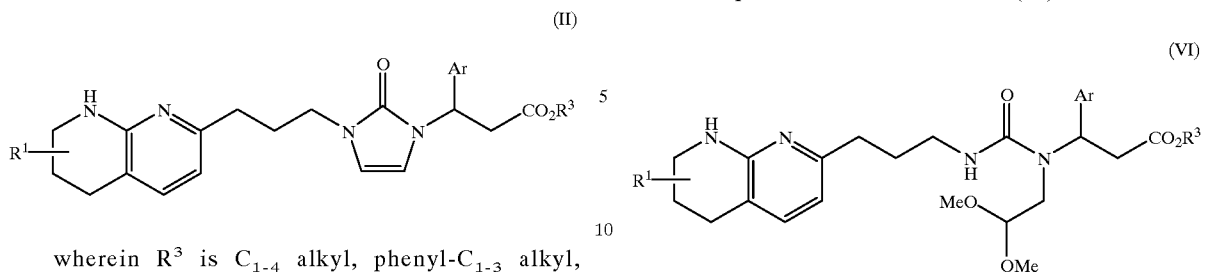

wherein R³ is $C_{1-4}$ alkyl, phenyl-$C_{1-3}$ alkyl, diphenylmethyl, or triphenylmethyl, to afford a compound of structural formula (VII);
(b) reducing the imidazolin-2-one double bond in a compound of structural formula (VII); and
(c) isolating the resulting product.

In another embodiment of the present invention, the imidazolin-2-one double bond in a compound of structural formula (II) is first reduced to afford a compound of structural formula (VIII) followed by cleavage of the R³ protecting group to afford a compound of structural formula (I).

In a class of these two embodiments, R³ is tert-butyl.

In a second class class of these two embodiments, R¹ is hydrogen and Ar is 6-methoxy-pyridin-3-yl. In a subclass of this class of these two embodiments, Ar is (S)-6-methoxy-pyridin-3-yl.

In a third class of these two embodiments, the imidazolin-2-one double bond is reduced by catalytic hydrogenation.

In a third embodiment of the present invention, there is provided a process for preparing a compound of structural formula (II):

(II)

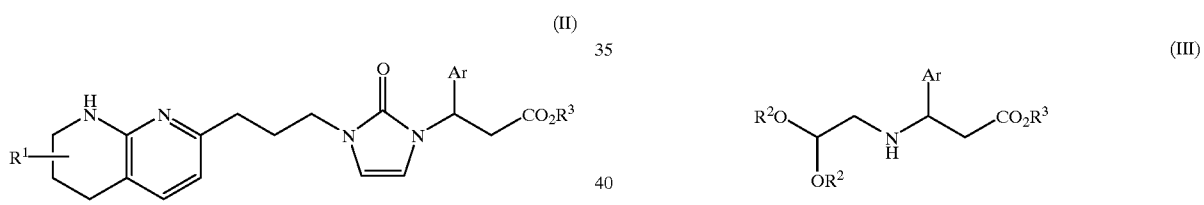

which comprises treating an amine of structural formula (III):

(III)

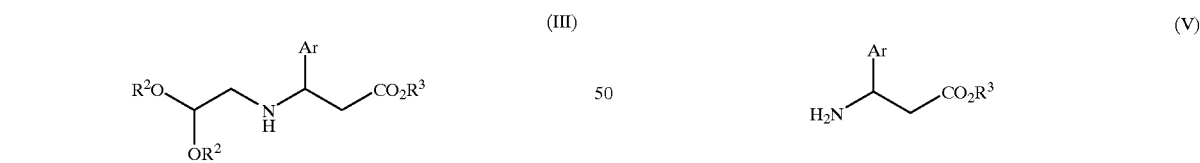

wherein R² is $C_{1-4}$ alkyl and R³ is $C_{1-4}$ alkyl, phenyl-$C_{1-3}$ alkyl, diphenylmethyl, or triphenylmethyl;
with an amine of structural formula (IV):

(IV)

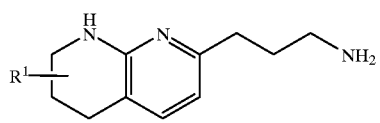

wherein R¹ is as defined above, in the presence of phosgene or a phosgene equivalent and base to produce a compound of structural formula (VI):

(VI)

followed by treatment with aqueous acid, and isolating the resulting product.

In a class of this embodiment, the phosgene equivalent is chlorocarbonic acid trichloromethyl ester or bis(trichloromethyl) carbonate (triphosgene). In a subclass of this class, the phosgene equivalent is bis(trichloromethyl) carbonate (triphosgene).

In another class of this embodiment, the base is an organic base, such as triethylamine, and the aqueous acid is aqueous sulfuric acid.

The preparation of compounds of structural formula (IV) is disclosed herein as well as in U.S. Pat. Nos. 5,952,341 and 6,048,861, WO 98/18460, and WO 99/31061.

In a fourth embodiment of the present invention, there is provided a process for producing a compound of structural formula (III):

(III)

by treating a compound of structural formula (V):

(V)

with glyoxal-1,1-di-$C_{1-4}$ alkyl acetal in the presence of a reducing agent, and isolating the resulting product.

In a class of this embodiment, glyoxal-1,1-di-$C_{1-4}$ alkyl acetal is glyoxal-1,1-dimethyl acetal.

In a second class of this embodiment, the reducing agent is sodium cyanoborohydride or sodium triacetoxyborohydride.

Further embodiments of this invention comprise the following novel compounds which are intermediates in the preparation of 3-4 and other compounds of structural formula (I):

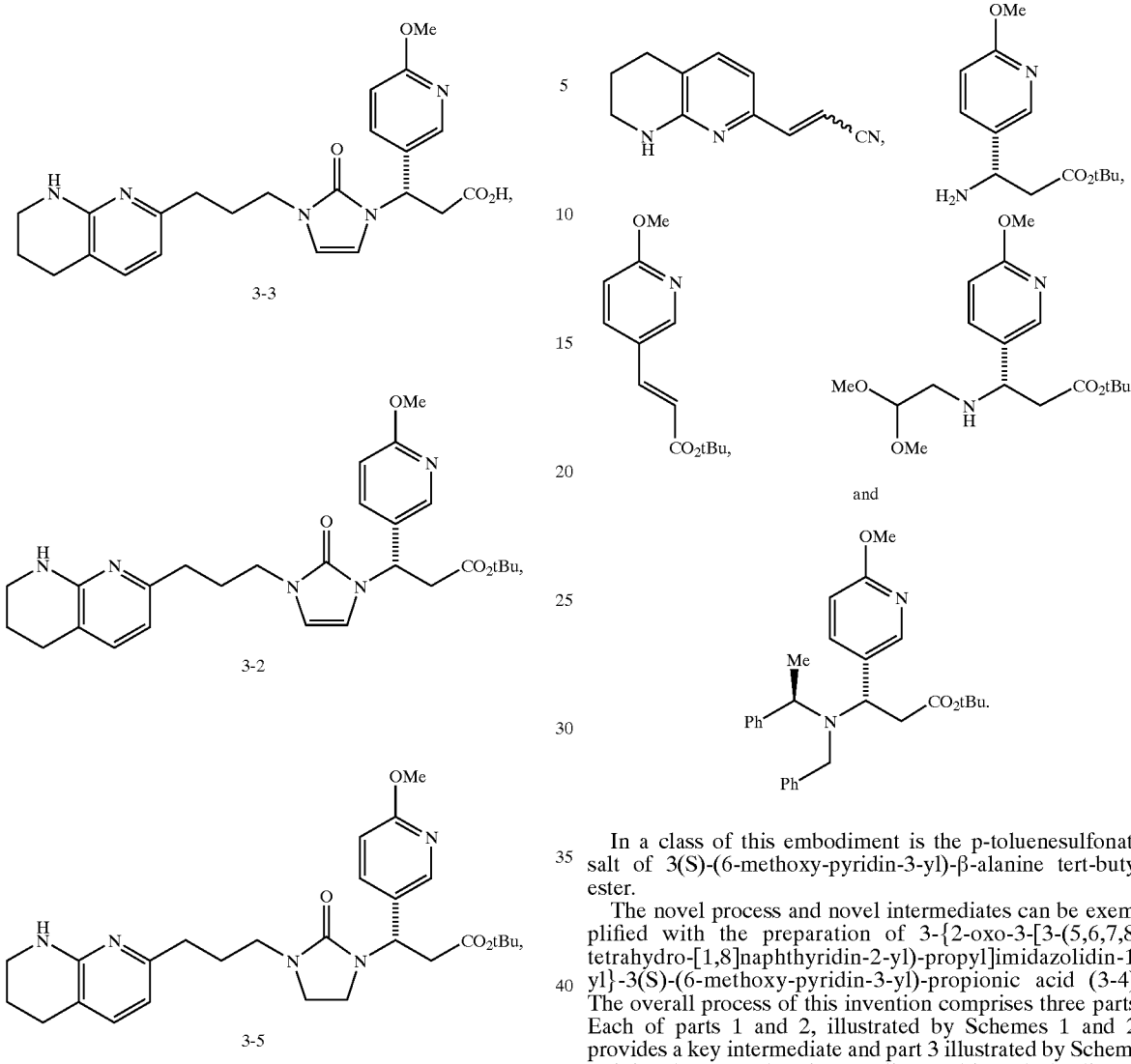

In a class of this embodiment is the p-toluenesulfonate salt of 3(S)-(6-methoxy-pyridin-3-yl)-β-alanine tert-butyl ester.

The novel process and novel intermediates can be exemplified with the preparation of 3-{2-oxo-3-[3-(5,6,7,8-tetrahydro-[1,8]naphthyridin-2-yl)-propyl]imidazolidin-1-yl}-3(S)-(6-methoxy-pyridin-3-yl)-propionic acid (3-4). The overall process of this invention comprises three parts. Each of parts 1 and 2, illustrated by Schemes 1 and 2, provides a key intermediate and part 3 illustrated by Scheme 3, joins these two key intermediates, ultimately leading to the desired compounds 3-3 and 3-4.

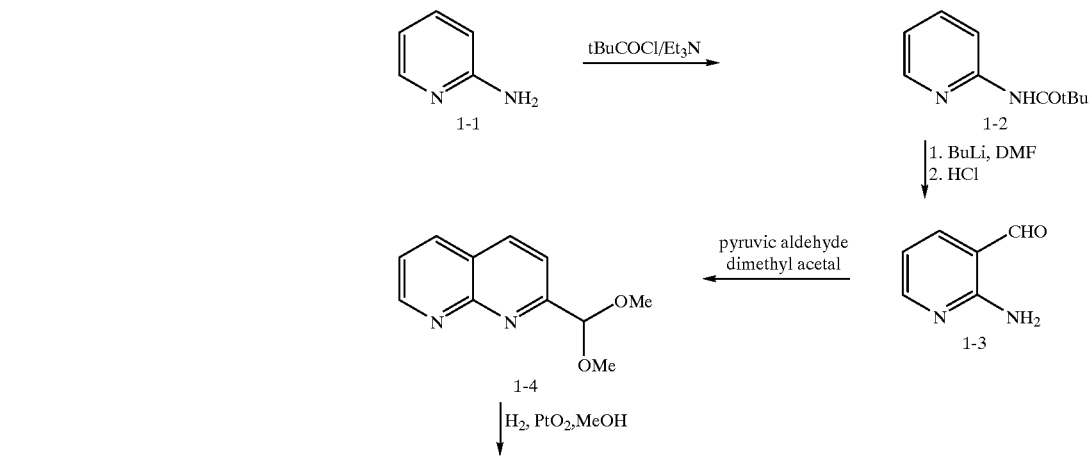

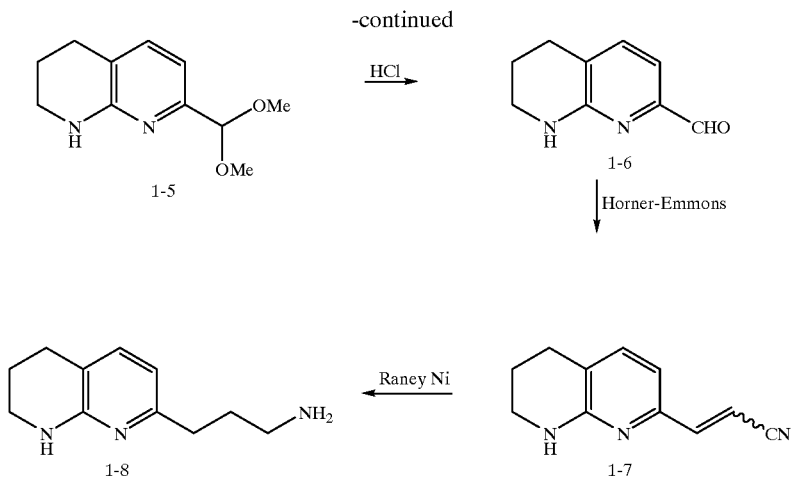

The known 2-amino-3-formyl-pyridine 1-3 is prepared as shown in Scheme 1 above. Compound 1-4 is prepared by a Friedlander reaction which comprises treatment of 1-3 in a solvent such an aqueous alcohol, for example aqueous methanol or ethanol, and pyruvic aldehyde dimethyl acetal at a temperature range of about 0° C. to about 55° C. with aqueous alkali such as 3–7 M sodium or potassium hydroxide. An alkali metal alkoxide, such as sodium, potassium, or lithium methoxide or ethoxide, or an organic base, such as piperidine or proline, may also employed as the base in the reaction. After aging for about 0.5 to about 2 hours, the product 1-4 is isolated.

Compound 1-5 is prepared by hydrogenating 1-4 in a solvent, such as a lower alkanol, for example, methanol or ethanol, in the presence of a noble metal catalyst such as $PtO_2$ at or about atmospheric pressure until hydrogen uptake ceases. Other catalysts which can be employed in the hydrogenation reaction include Raney nickel, Pd/C, Rh/C, Ru/C, $Pd/Al_2O_3$, Pt/C, $Pt/Al_2O_3$, $Rh/Al_2O_3$, and $Ru/Al_2O_3$.

Compound 1-5 is treated with aqueous HCl, and the mixture is heated from about 75° C. to about 95° C. for about 1–4 hours. Other acids which can be used in the hydrolysis reaction include sulfuric acid, trifluoroacetic acid, and methanesulfonic acid. After cooling, isopropyl acetate (iPAc) is added, and the mixture is made slightly alkaline with aqueous alkali, and the product 1-6 is isolated by liquid/liquid extraction.

The preparation of compounds 1-4, 1-5, and 1-6 has also been described in U.S. Pat. No. 5,981,546 and WO 98/08840 (published March 5, 1998) using variants of the above conditions.

Compound 1-7 is prepared via a Wittig reaction, such as the Homer-Emmons modification, by treatment of a solution of compound 1-6 and diethyl (cyanomethyl)phosphonate in a suitable solvent, such as THF and toluene, with a strong alkali metal hydroxide, such as sodium hydroxide, followed by continued stirring for about 0.5–2 hours. Other bases, such an alkyl lithium, sodium methoxide, potassium tert-butoxide, lithium diisopropylarnide, lithium or sodium hexamethyldisilazide, or alkylmagnesium halide, may also be used in place of the alkali metal hydroxide. The reaction can be carried out at a temperature range of about –80° C. to 110° C. The product 1-7 is isolated by dilution with iPAc and separation of the organic layer.

The key intermediate 1-8 is prepared by treating a suspension of 1-7 in saturated aqueous ammonium hydroxide with hydrogen gas under medium to high pressure in the presence of a Raney nickel 2800 catalyst. For each mole of nitrile 1-7, there is employed about 1.5 to about 3 moles of ammonium hydroxide solution. Other catalysts which can be used in the reduction include Pd/C, $Pd(OH)_2/C$, $Pd/Al_2O_3$, Pt/C, $Pt/Al_2O_3$, $PtO_2$, $Rh/Al_2O_3$, and Raney nickel 3111, 5601, 2700, and 2724.

Intermediate 1-8 can also be prepared following the procedures disclosed in U.S. Pat. No. 6,048,861, which is incorporated by reference herein in its entirety.

Scheme 2

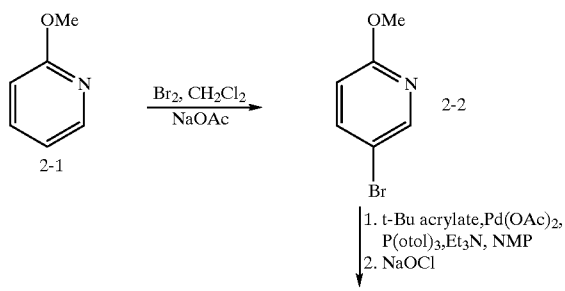

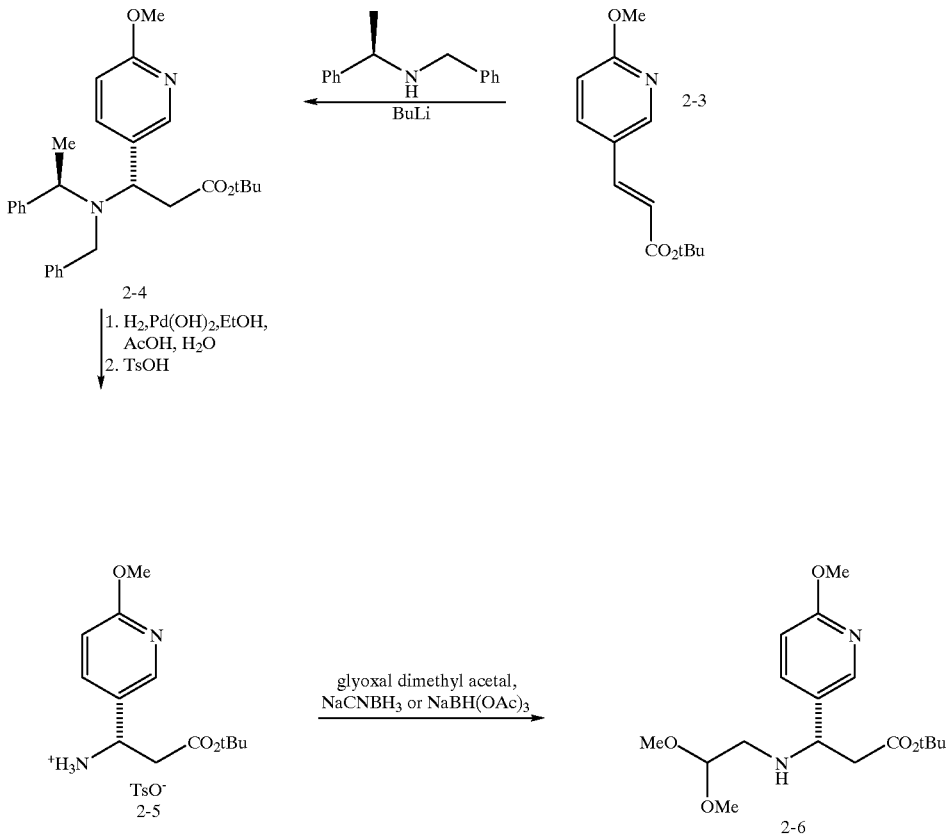

As shown in Scheme 2 above, compound 2-1 is brominated by treatment with bromine in an organic solvent such as methylene chloride, chloroform, 1,2-dichloroethane, or the like, in the presence of sodium acetate at a temperature below about 10° C. to yield compound 2-2.

Compound 2-2 is converted to compound 2-3 in a Heck-type procedure by adding it to a mixture comprised of an alkyl acrylate, such as methyl, ethyl, or t-butyl acrylate, in the presence of a strong organic base such as triethylamine, in a solvent such as N,N-dimethylformamide (DMF) or N-methylpyrrolidinone (NMP), a phosphine ligand such as triphenylphosphine or tri-o-tolylphosphine, and a palladium catalyst such as palladium acetate, and heating the mixture at about 80° C. to about 125° C. In one embodiment of the Heck reaction, the temperature is maintained at 90–95° C. Oxidation of the phosphine with a solution of sodium hypochlorite (NaOCl) to the phosphine oxide allows for simple removal of the phosphine oxide from the Heck reaction mixture by filtering through a pad of silica gel.

Compound 2-4 is formed by a chiral Michael addition of the lithium amide derived from N-benzyl-(R)-2-methylbenzylamine and n-butyllithium to compound 2-2 in an organic solvent, such as tetrahydrofuran, at about −70° C. to −40° C. These conditions have been described by Davies et al. in *Tetrahedron: Asymmetry*, Vol.2, pp.183–186, 1991.

Other bases, such as n-hexyl lithium, may also be used in place of n-butyl lithium. Use of N-benzyl-(S)-2-methylbenzylamine in place of N-benzyl-(R)-2-methylbenzylamine affords the 3(R)-diastereoisomer of 2-4.

Compound 2-5 is obtained by reduction of compound 2-4 with $H_2$ at about 40 psi and 20% $Pd(OH)_2$ in ethanol and acetic acid. After removal of the catalyst and evaporation of the ethanol, the resulting amine is then treated with a solution of para-toluenesulfonic acid in an ethereal solvent, such as methyl t-butyl ether (MTBE), to form the para-toluenesulfonate (p-TSA) salt 2-5. The p-TSA salt was found to be highly crystalline, and crystallization of this salt was found to enhance the enantiomeric purity of 2-5.

The key intermediate 2-6 and the process for its synthesis form separate embodiments of this invention. The process comprises a two-carbon homologation by reductive alkylation of the amine 2-5 with glyoxal-1,1-di-$C_{1-4}$ alkyl acetal, under the influence of a complex metal hydride in water, an organic solvent, or aqueous organic solvent, such as aqueous THF or aqueous methanol. The complex metal hydride, such as $NaBH_3CN$, $Na(OAc)_3BH$, sodium borohydride, or tetrabutylammonium borohydride, is either added as a solid portionwise or taken up in an organic solvent such as methanol, ethanol, acetic acid, tetrahydrofuran, or dichloromethane and added to the reaction mixture.

Scheme 3

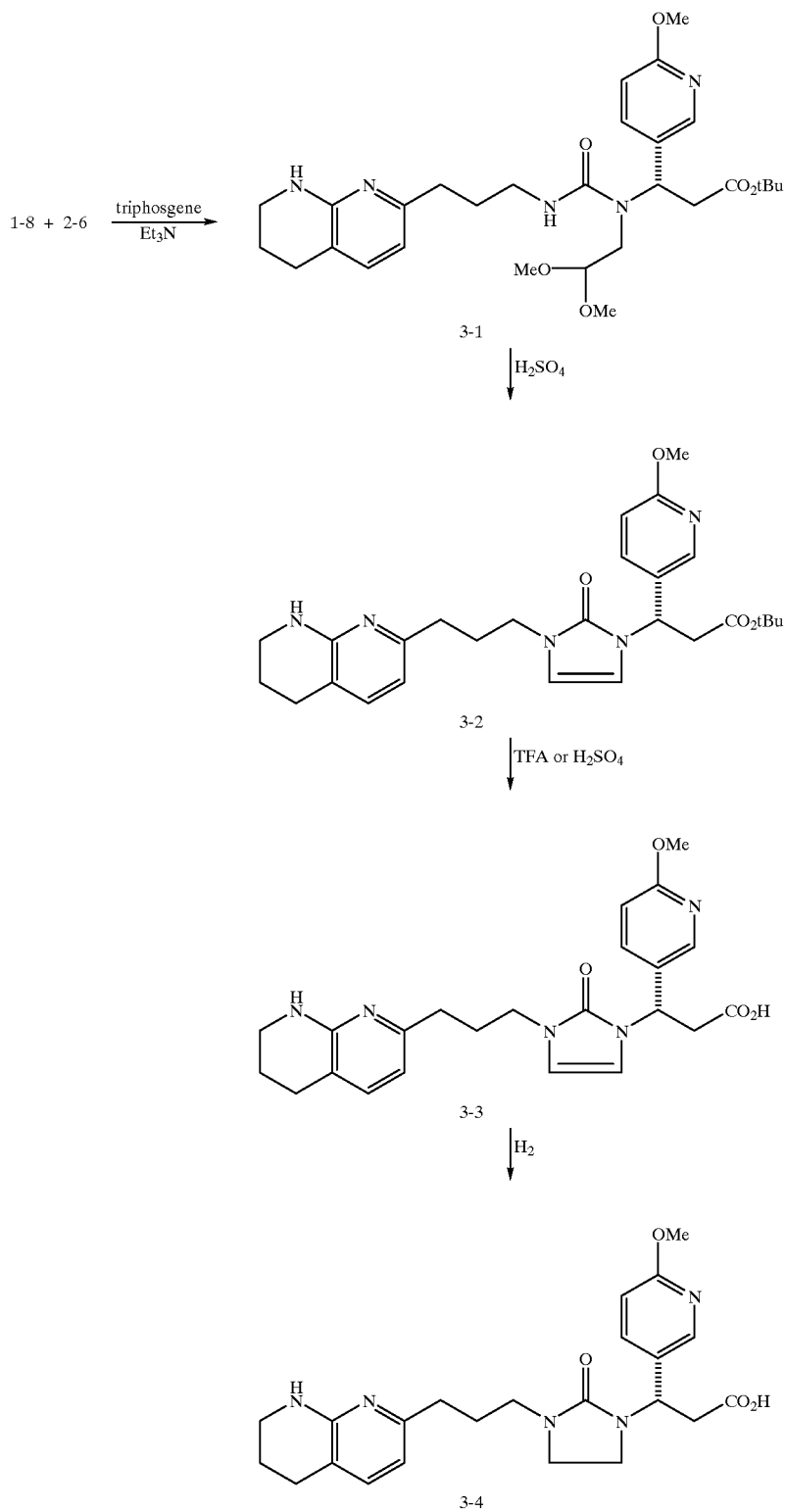

In reaction Scheme 3, a mixture of the acetal 2-6 and triethylamine in anhydrous THF is slowly added to a cold (−15° C. to 15° C.) solution of bis(trichloromethyl) carbonate (triphosgene) in anhydrous THF while keeping the temperature below about 0° C. to about 10° C. Phosgene or another phosgene equivalent, such as chlorocarbonic acid trichloromethyl ester, may also be used in place of triphosgene. After aging, the reaction mixture is kept at that temperature for about 15 to 45 minutes and then at about room temperature for another 15 to 45 minutes, the excess triphosgene is purged and the amine 1-8 and a base, such as triethylamine, are added at about 0° C. to about 10° C. and the suspension is stirred at about 30° C. to 50° C. for about 5 to 7 hours. Compound 3-1, produced by the above process, is used directly in the synthesis of compound 3-2. The reaction mixture is cooled to room temperature, aqueous acid, such as aqueous sulfuric acid or aqueous hydrochloric acid, is added, the mixture is stirred for about 8 to 12 hours and then added to a mixture of iPAc and aqueous sulfuric acid or hydrochloric acid and the product 3-2 is isolated by solvent/solvent extraction after adjusting the pH.

The t-butyl ester group of 3-2 is cleaved to yield 3-3 by treatment with an acid such as trifluoroacetic acid, formic acid, sulfuric acid, hydrochloric acid, p-toluenesulfonic acid, or the like, at a temperature from about room temperature to about 50° C. until the reaction is complete, usually about 3 to 6 hours. Compound 3-3 was found to be highly crystalline, which allowed for enhancement of the enantiomeric and chemical purity of the final product 3-4 at the penultimate stage of the reaction sequence. Crystalline 3-3 obtained from solutions containing water and acetone exhibited three distinct X-ray powder diffraction patterns (I, II, and III) depending upon the water content in the crystals: Pattern I (with characteristic diffraction peaks corresponding to d-spacings of 3.4, 3.5, 4.9, 5.3, 6.2 and 8.1 angstroms) was observed for crystals with water content in the range of 5 to 9%; Pattern II (with characteristic diffraction peaks corresponding to d-spacings of 3.5, 3.6, 4.8, 5.5, 6.0, and 8.3 angstroms) was observed for crystals with water content in the range of 13 to 16%; and Pattern III (with characteristic diffraction peaks corresponding to d-spacings of 3.4, 3.5, 3.6, 3.8, 4.1, 5.0 and 15.7 angstroms) was observed for crystals with water content in the range of 33 to 41%. Crystalline 3-3 obtained from solutions containing water and isopropanol exhibited patterns having characteristic diffraction peaks corresponding to d-spacings of 3.5, 3.8–3.9, 4.4, 4.5-4.6, 6.4 and 18.9–19.0 angstroms. In addition, each of these patterns contained a peak corresponding to a d-spacing in the vicinity of 12.6 to 15.7 angstroms, depending on the water content of the crystal. Crystals containing 2.3% water showed a peak at 12.6 angstroms (pattern IV); crystals containing about 3.3% water displayed a peak at 13.0 angstroms (pattern V); and crystals containing higher levels of residual solvent showed a peak at 15.7 angstroms (pattern VI).

Compound 3-4 is produced by reducing the double bond in 3-3, such as by hydrogenation in a solvent such as water, aqueous methanol, or aqueous ethanol, with hydrogen at medium pressure in the presence of an alkali metal hydroxide, such as sodium or potassium hydroxide, or an amine base, such as ammonia or an alkylamine, for example, triethylamine, in the presence of a noble catalyst such as palladium hydroxide on carbon, palladium black, or palladium-on-charcoal.

When crystallized from water, filtered, and dried at room temperature under nitrogen for up to about 24 hours, compound 3-4 is obtained in the form of a hemihydrate as evidenced by Karl-Fischer titration and thermogravimetric analysis (TGA). The crystalline hemihydrate is characterized by the positions and intensities of the major peaks in the X-ray powder diffraction pattern as well as its FT-IR spectrum.

Compound 3-4 may also be prepared as shown in the Scheme below by first reducing the double bond in 3-2 under the conditions described above to afford saturated t-butyl ester 3-5 and then cleaving the t-butyl ester group in 3-5 to give 3-4 under the conditions described above.

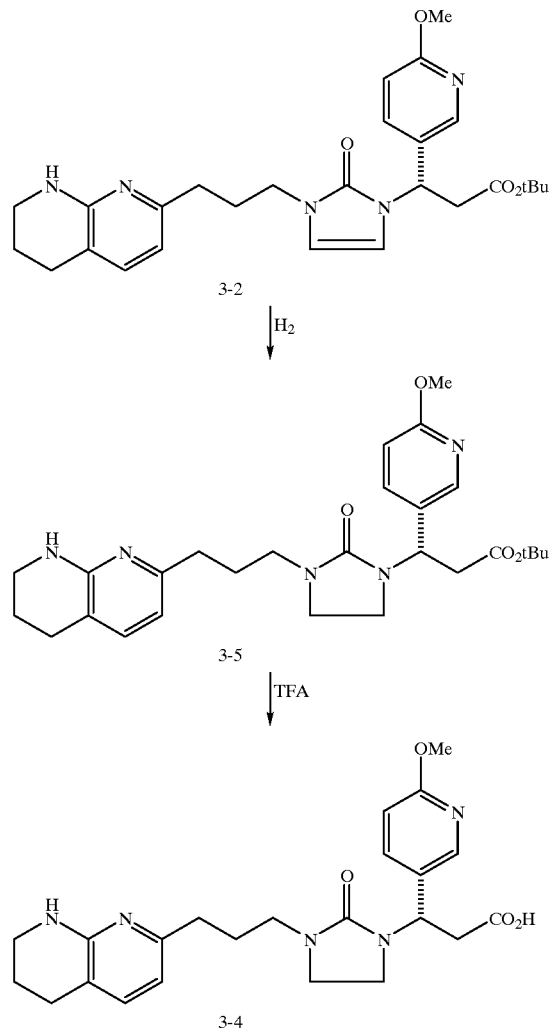

Representative experimental procedures utilizing the novel process are detailed below. For purposes of illustration, the following Example is directed to the preparation of compounds 3-3 and 3-4, but doing so is not intended to limit the present invention to a process for making those specific compounds.

Abbreviations: AcOH is acetic acid; BuLi is n-butyl lithium, $CH_2Cl_2$ is dichloromethane; EtOAc is ethyl acetate; $Et_3N$ is triethylamine; iPAc is isopropyl acetate; MTBE is methyl t-butyl ether; NMP is N-methylpyrrolidinone; NaOCl is sodium hypochlorite; NMR is nuclear magnetic resonance; $Na_2CO_3$ is sodium carbonate; $NaHCO_3$ is sodium hydrogencarbonate; $NaCNBH_3$ is sodium cyanoborohydride; $NaBH(OAc)_3$ is sodium triacetoxyborohydride; $PtO_2$ is platinum oxide; $P(otol)_3$ is tri-o-tolylphosphine; p-TsOH is para-toluenesulfonic acid; and THF is tetrahydrofuran.

By halogen is meant fluorine, chlorine, bromine, or iodine.

The FT-IR spectrum of 3-4 was obtained on a Nicolet 510P Fourier-Transform infrared spectrometer.

The differential scanning calorimeter (DSC) curve was taken on a TA 2910 Differential Scanning Calorimeter with a heating rate of 10° C./minute under nitrogen.

EXAMPLE

3-{2-Oxo-3-[3-(5,6,7,8-tetrahydro-[1,8]naphthyridin-2-yl)-propyl]imidazolidin-1-yl}-3(S)-(6-methoxy-pyridin-3-yl)-propionic acid (3-4)

Step A: Preparation of Compound 1-4

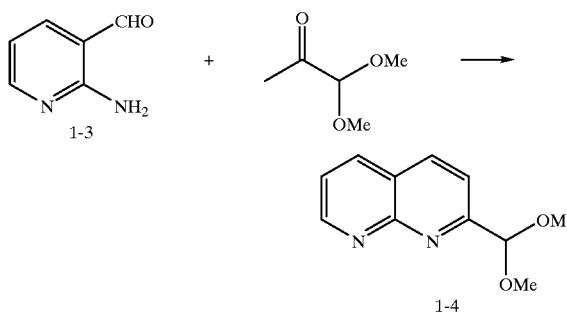

To a cold (6° C.) solution of 2-amino-3-formylpyridine 1-3 (40 g, 0.316 mol), ethanol (267 ml), water (41 ml), and pyruvic aldehyde dimethyl acetal (51.3 ml, 0.411 mol) was added 5 M NaOH (82.3 ml, 0.411 mol) at a rate such that the internal temperature was lower than 20° C. After stirring at ambient temperature for 1 hour, the ethanol was removed under vacuum, and iPAc (100 mL) and NaCl (55 g) were added. The layers were separated and the aqueous layer was extracted with iPAc (2×100 ml). The organic layers were combined, filtered through a silica gel bed (90 g), followed by rinse with iPAc (1 L). The fractions were combined and concentrated to 200 ml at 38° C. To the solution was slowly added hexane (400 ml). The resulting suspension was cooled to 10° C. and aged for 30 min before filtration. The suspension was filtered and dried under vacuum to give the product 1-4 (54.2 g; 84%) as colorless crystals; m.p. 53.5–55.5° C. To the mother liquors was added additional hexane (100 mL), and another 7.2 g (11%) of 1-4 was isolated after filtration.

$^1$H NMR (300 MHz; CDCl$_3$): δ 8.89 (dd, J=4.3 and 2.0 Hz, 1H), 8.03 (d, J=8.4 Hz, 1H), 7.98 (dd, J=8.1 and 2.0 Hz, 1H), 7.56 (d, J=8.4 Hz, 1H), 7.26 (dd, J=8.1 and 4.3 Hz, 1H), 5.28 (s, 1H), and 3.30 (s, 6H). $^{13}$C NMR (75.5 MHz; CDCl$_3$): δ 161.3, 155.0, 153.5, 137.9, 136.8, 122.5, 122.3, 119.4, 105.9, and 54.9.

Step B: Preparation of Compound 1-5

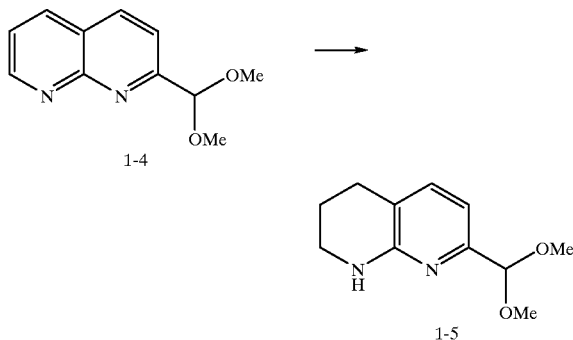

A solution of the acetal 1-4 (20.0 g; 97.9 mmol) in ethanol (400 mL) was hydrogenated in the presence of PtO$_2$ (778 mg) under one atmosphere pressure of hydrogen at room temperature for 18 hours. The reaction mixture was filtered through Solka Flok and washed with a mixture of ethanol-H$_2$O (1:2 v/v). The filtrate and washings were combined and concentrated in vacuo to remove ethanol. The product crystallized as the ethanol was removed. The crystals were filtered and dried in vacuo to give product 1-5 (18.7 g, 92%); m.p. 91–92.5° C. $^1$H NMR (300 MHz; CDCl$_3$): δ 7.08 (d, J=7.4 Hz, 1H), 6.62 (d, J=7.4 Hz, 1H), 5.07 (s, 2H; 1H exchangeable with D$_2$O),3.37–3.29 (m, 2H), 3.29 (s, 6H), 2.64 (t, J=6.3 Hz, 2H), and 1.86–1.78 (m, 2H). $^{13}$C NMR (75.5 MHz; CDCl$_3$): δ 155.9, 153.0, 136.3, 116.0, 109.8, 103.9, 53.3, 41.5, 26.6, and 21.2.

Step C: Preparation of Compound 1-6

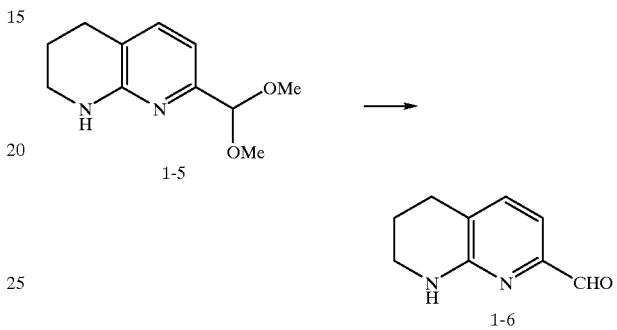

To a mixture of the acetal 1-5 (35 g, 0.16 mol) in cold water (~5° C., 90 ml) was added concentrated aqueous HCl (30 ml, 0.36 mol). The resulting solution was heated at 85° C. for 2.5 h. After the reaction was cooled to 13° C., iPAc (60 ml) was added. To the mixture was added aqueous NaOH (50 wt %) slowly to about pH 11, keeping the internal temperature below 25° C. The layers were separated and the aqueous layer was extracted with iPAc (2×120 ml). The organic layers were combined and concentrated in vacuo to give a reddish oil (26 g; 87.5 wt %; 95.3%) which was used in next reaction without further purification. An authentic sample was prepared by crystallization from THF; m.p. 63.5–64° C.

$^1$H NMR (300 MHz; CDCl$_3$): δ 9.70 (s, 1H), 7.17 (d, J=7.3 Hz, 1H), 7.03 (d, J=7.3 Hz, 1H), 5.94 (bs, 1H), 3.39–3.33 (m, 2H), 2.69 (t, J=6.3 Hz, 2H), and 1.84–1.80 (m, 2H). $^{13}$C NMR (75.5 MHz; CDCl$_3$): δ 192.8, 156.8, 149.5, 136.2, 122.5, 113.4, 41.4, 27.2, and 20.6.

Step D: Preparation of Compound 1-7

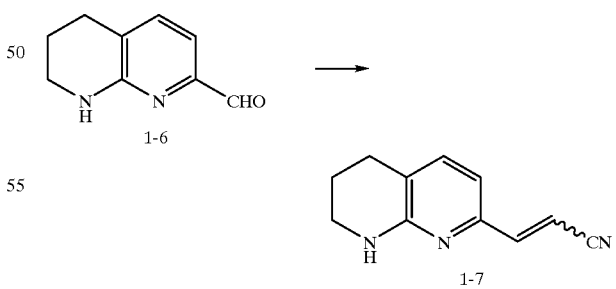

To a solution of the aldehyde 1-6 (26.0 g, 87.5 wt %; 140 mmol) and diethyl (cyanomethyl)phosphonate (26.7 mL; 140 mmol) in THF (260 ml) was added 50 wt % aqueous NaOH (14.8 g; 174 mmol) at a rate such that the internal temperature was below 26° C. After stirring at room temperature 1 hour, 260 ml of iPAc was added. The organic layer was separated and concentrated in vacuo to give 1-7 as a yellow solid (31.6g, 84.6 wt %, 90% yield from 1-5, trans:cis ~9: 1). Authentic samples (trans and cis) were purified by silica gel column chromatography. trans-1-7: m.p. 103.7–104.2° C.; $^1$H NMR (300 MHz; CDCl$_3$): δ 7.14 (d, J=16.0 Hz, 1H), 7.12 (d, J=7.2 Hz, 1H), 6.48 (d, J=7.2 Hz, 1H), 6.33 (d, J=16.0 Hz, 1H), 5.12 (bs, 1H), 3.41–3.36 (m,2H 2.72 (t, J=6.3 Hz, 2H), and 1.93–1.84 (m, 2H). $^{13}$C NMR (75.5 MHz; CDCl$_3$): δ 156.1, 149.4, 147.4, 136.3, 120.1, 118.8, 114.8, 97.7, 41.4, 27.0, and 21.0. cis-1-7: $^1$H NMR (300 MHz; CDCl$_3$): δ 7.09 (d, J=7.3 Hz, 1H), 6.87 (d, J=11.8 Hz, 1H), 6.73 (d, J=7.3 Hz, 1H), 5.35 (d, J=11.8 Hz, 1H), 3.37–3.33 (m, 2H), 2.69 (t, J=6.3 Hz, 2H), and 1.90–1.81 (m, 2H). $^{13}$C NMR (75.5 MHz; CDCl$_3$): δ 155.5, 147.8, 147.4, 136.0, 119.1, 117.3, 114.2, 95.8, 41.2, 26.7, and 20.8.

Step E: Preparation of Compound 1-8

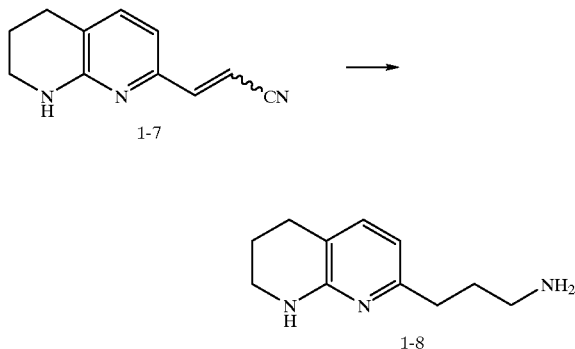

A slurry of the nitrile 1-7 (648 g; 3.5 mol) and saturated aqueous ammonium hydroxide (7 L) was hydrogenated under 40 psi of hydrogen at 50° C. for 16 h in the presence of Raney nickel 2800 (972 g). The mixture was filtered through Solka Flok and the pad was rinsed with water (2×1 L). After addition of NaCl (3.2 kg), the mixture was extracted with CH$_2$Cl$_2$ (3×5 L). The combined organic phases were concentrated to an oil. The oil was dissolved in MTBE (1 L) and seeded. The suspension was slowly evaporated to provide the amine 1-8 as a colorless crystalline solid (577g; 89%); m.p. 66.0–68.5° C.

$^1$H NMR (400 MHz; CDCl$_3$): δ 7.03 (d, J=7.3 Hz, 1H), 6.33 (d, J=7.3 Hz, 1H), 4.88 (bs, 1H), 3.37 (t, J=5.3 Hz, 2H), 2.72 (t, J=6.9 Hz, 2H), 2.67 (t, J=6.3 Hz, 2H), 2.57 (t, J=7.5 Hz, 2H), 1.92–1.74 (m, 6H). $^{13}$C NMR (101 MHz; CDCl$_3$): δ 157.9, 155.7, 136.6, 113.1, 111.2, 41.8, 41.5, 35.1, 33.7, 26.3, and 21.5.

Step F: Preparation of Compound 2-2

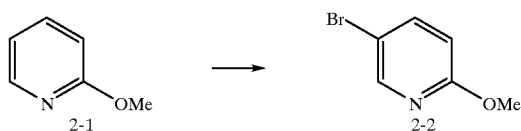

To a suspension of 2-methoxypyridine (2-1) (3.96 kg; 36.3 mol), NaOAc (3.57 kg; 39.9 mol), and dichloromethane (22 L) was added a solution of bromine (2.06 L; 39.9 mol) in dichloromethane (2 L), maintaining the reaction temperature below 7° C. over 2–3 hours. The mixture was aged for 1 hour at 0° C.–7° C. and stirred at room temperature overnight. The reaction mixture was filtered and rinsed with dichloromethane (about 5 L) (the filtration step may be omitted without negatively impacting the yield). The filtrate and washings were combined, washed with cold 2 M NaOH (22 L; pH is maintained between 9 and 10) maintaining the temperature below 10° C., and with cold water (11 L). The organic layer was separated and concentrated under reduced pressure to give crude product 2-2 (6.65 kg). The crude product 2-2 was purified by vacuum distillation to give pure 2-2 (5.90 kg, 86%). (Reference: G. Butora et al., J. Amer. Chem. Soc. 1997, 119, 7694–7701).

$^1$H NMR (250 MHz; CDCl$_3$): δ 8.18 (d, J=2.5 Hz, 1H), 7.61 (dd, J=8.8 and 2.5 Hz, 1H), 6.64 (d, J=8.8 Hz, 1H), and 3.89 (s, 3H). $^{13}$C NMR (62.9 MHz; CDCl$_3$): δ 162.9, 147.5, 141.0, 112.6, 111.7, and 53.7.

Step G: Preparation of Compound 2-3

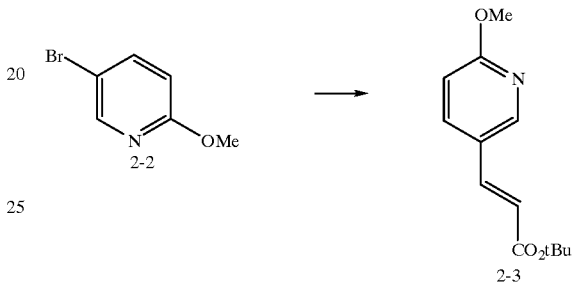

A mixture of tert-butyl acrylate (98%; 137 mL; 916 mmol), triethylamine (100 mL; 720 mmol), tri-O-tolylphosphine (97%; 6.30 g; 20 mmol), Pd(OAc)$_2$ (1.80 g; 8 mmol), and NMP (90 mL) was degassed three times. The mixture was heated to 90° C. and a solution of 2-methoxy-5-bromopyridine 2-2 (50.0 g; 266 mmol) and NMP (10 mL) was added via addition funnel over 1 hour, maintaining the reaction temperature at 90° C. The reaction was heated for 12 hours after complete addition. The reaction mixture was cooled down to room temperature after completion of the reaction. To the reaction mixture was added toluene (400 mL) and the resulting solution was then passed through a pad of Solka Flok. The filter cake was washed with toluene (270 mL). The toluene solution was washed three times with water (540 mL, each). An aqueous solution of NaOCl (2.5%; 200 mL) was slowly added to the toluene solution keeping the temperature about 30° C. The reaction was aged 50 min with vigorous stirring. The organic layer was separated, washed with water (540 mL) three times, and followed by saturated aqueous NaCl (270 mL). The organic layer was concentrated to an oil. The oil was dissolved in 270 ML hexanes and loaded onto a silica gel (90 g) pad. The silica gel pad was washed with hexanes (73 mL). The product 2–3 was eluted with EtOAc: hexane (1:8; v/v) in about 730 mL. The yellow solution was concentrated to an oil (126 g; 49.2 wt %; 98.4% yield). The crude oil was used for the next reaction without further purification. Authentic crystalline material was obtained by further concentration of the oil; m.p. 44–45° C.

$^1$H NMR (250 MHz; CDCl$_3$): δ 8.23 (d, J=2.4 Hz, 1H), 7.73 (dd, J=8.7 and 2.4 Hz, 1H), 7.50 (d, J=16.0 Hz, 1H), 6.73 (d, J=8.7 Hz, 1H), 6.25 (d, J=16.0 Hz, 3.94 (s, 3H), and 1.51 (s, 9H). $^{13}$C NMR (62.9 MHz; CDCl$_3$): δ 166.1, 165.1, 148.1, 139.9, 136.3, 124.0, 119.1, 111.5, 80.6, 53.7, and 28.2.

Step H: Preparation of Compound 2-4

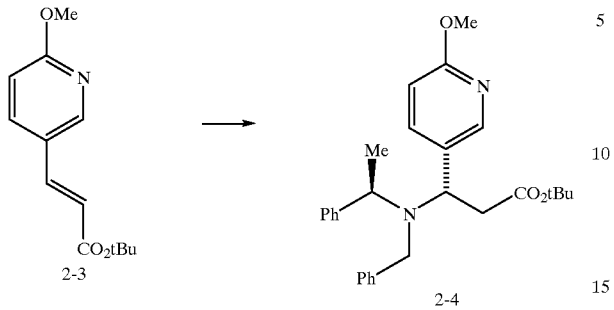

To a solution of (R)-(+)-N-benzyl--methylbenzylamine (88 mL; 0.42 mol) and anhydrous THF (1 L) was added n-BuLi (2.5 M in hexanes; 162 mL; 0.41 mol) over 1 hour at −30° C. The solution was then cooled to −65° C. A solution of t-butyl ester 2–3 (65.9 g; 0.28 mol) in anhydrous THF (0.5 L) was added over 90 minutes during which the temperature rose to −57° C. After the reaction was complete, the reaction solution was poured into a mixture of saturated aqueous NH$_4$Cl (110 mL) and EtOAc (110 mL). The organic layer was separated, washed separately with aqueous AcOH (10%; 110 mL), water (110 mL) and saturated aqueous NaCl (55 mL). The organic layer was concentrated in vacuo to a crude oil. The crude oil was purified by passing through a silica gel (280 g) pad eluting with a mixture of EtOAc and hexanes (5:95). The fractions containing the product were combined and concentrated in vacuo to give a thick oil. The resulting oil was used directly in the next step. The oil contained 91 g (0.20 mol, 73% yield) of the product 2-4.

$^1$H NMR (400 MHz; CDCl$_3$): δ 8.16 (d, J=2.4 Hz, 1H), 7.65 (dd, J=8.8 and 2.4 Hz, 1H), 7.40 (m, 2H), 7.34 (m, 2H), 7.30–7.16 (m, 6 H), 6.74 (d, J=8.8 Hz, 1H), 4.39 (dd, J=9.8 and 5.3 Hz, 1H), 3.97 (q, J=6.6 Hz, 1H), 3.94 (s, 3H), 3.67 (s, 2H), 2.52 (dd, J=14.9 and 5.3 Hz, 1H), 2.46 (dd, J=14.9 and 9.8 Hz, 1H), 1.30 (d, J=6.6 Hz, 3H), and 1.26 (s, 9H); $^{13}$C NMR (101 MHz; CDCl$_3$): δ 170.8, 163.3, 146.4, 143.8, 141.3, 138.6, 130.0, 128.24, 128.19, 127.9, 127.7, 127.0, 126.6, 110.4, 80.5, 57.4, 56.6, 53.4, 50.7, 37.5, 27.8, and 17.3.

Step I: Preparation of Compound 2-5

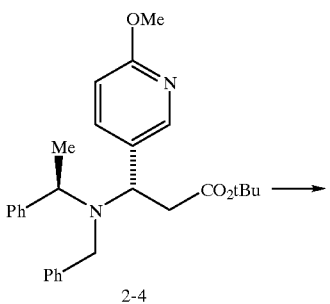

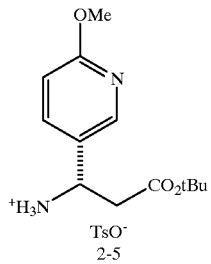

The thick oil (2–4; containing 80.3 g; 0.18 mol) was hydrogenated in the presence of Pd(OH)$_2$ (20 wt % on carbon; 8.0 g) in a mixture of EtOH (400 mL), AcOH (40 mL), water (2 mL) under 40 psi of hydrogen at 35° C. for 8 hours. The reaction mixture was filtered through a pad of Solka Flok, evaporated to a thick oil in vacuo, and flushed with MTBE (2 L each) several times. Upon cooling, the batch solidified to a thick white solid. The thick slurry was heated to 50° C. and the solids dissolved. A hot solution (40° C.) of p-TsOH (41.7 g; 0.22 mol) and MTBE (400 mL) was then transferred slowly to the warm solution of the amine. After about 30% of the p-TsOH solution had been added, the solution was seeded and a thick slurry formed. The addition was continued and was complete in 2 hours. The solution was aged after completion of the addition for 3 hours at 45° C. The solution was then slowly cooled to room temperature. The solution was aged for 12 hours at room temperature and then cooled to 6° C. The very thick slurry was filtered, washed with MTBE (100 mL) and dried under vacuum at 35° C. for several days to give the product 2-5 (71.0 g; 73%); mp: 142×144° C. $^1$H NMR (400 MHz; CDCl$_3$): δ 8.40 (bs, 3H), 8.22 (s, 1H), 7.87 (d, J=8.8 Hz, 1H), 7.56 (d, J=8.0 Hz, 2H), 7.11 (d, J=8.0 Hz, 2H), 6.65 (d, J=8.8 Hz, 1H), 4.63 (m, 1H), 3.91 (s, 3H), 3.09 (dd, J=16.5 and 6.0 Hz, 1H), 2.87 (dd, J=16.5 and 8.8 Hz 1H), 2.36 (s, 3H), and 1.27 (s, 9H); $^{13}$C NMR (101 MHz; CDCl$_3$): δ 168.4, 164.2, 146.8, 140.9, 140.4, 137.8, 128.8, 125.8, 124.3, 111.0, 81.6, 53.5, 49.6, 39.3, 27.8, and 21.3.

Step J: Preparation of Compound 2-6

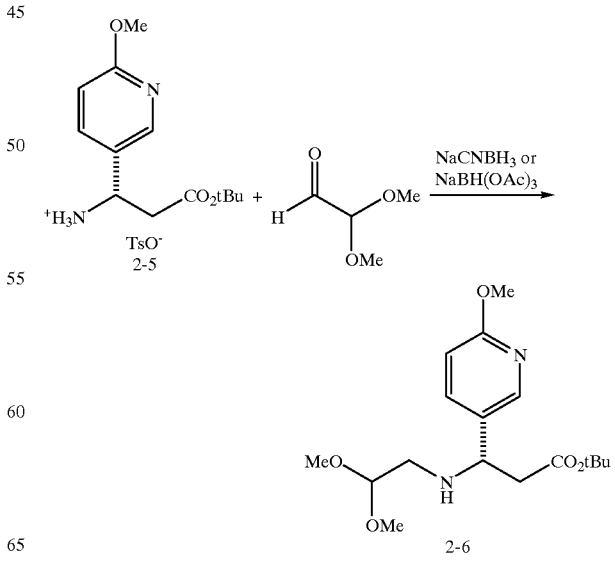

Method A: Reductive amination with sodium cyanoborohydride

To a mixture of p-TSA salt 2-5 (50 g; 0.118 mol), MeOH (300 mL), and glyoxal-1,1-dimethyl acetal (45 wt % in MTBE; 40 g; 0.165 mol) was slowly added a solution of $NaBH_3CN$ (9.35 g; 0.141 mol; 95%) in MeOH (50 mL). The rate of addition was such that the temperature never exceeded 3.5° C. (over 50 min). The reaction mixture was allowed to warm up to ambient temperature. After reaction completion (4–5 hours, final batch temperature was 16° C.), ice was placed around the flask and aqueous $NaHCO_3$ (14.8 g in 200 mL of $H_2O$) solution was added slowly. The mixture was concentrated to 420 mL. Additional $H_2O$ (200 mL) and EtOAc (500 mL) were added. The aqueous layer was separated and extracted with EtOAc (500 mL). The organic layers were combined, dried over $MgSO_4$, and concentrated to approximately 100 mL. The resulting solution was passed through a small silica gel pad followed by additional 300 mL of EtOAc. The fractions containing 2-6 were combined and concentrated in vacuo to give 46.2 g of product 2-6 (46.2 g; 90.4 wt %; 92%) as an oil. This compound was used for the next step without further purification. An authentic sample was prepared by silica gel column chromatography. $^1$H NMR (400 MHz; $CDCl_3$): δ 8.08 (d, J=2.4 Hz, 1H), 7.61 (dd, J=8.4 and 2.4 Hz, 1H), 6.73 (d, J=8.4 Hz, 1H), 4.41 (t, J=5.6 Hz, 1H), 4.00 (dd, J=8.2 and 6.0 Hz, 1H), 3.93 (s, 3H), 3.35 (s, 3H), 3.31 (s, 3H), 2.67 (dd, J=15.3 and 8.2 Hz, 1H), 2.60 (dd, J=12.0 and 5.6 Hz, 1H), 2.51 (dd, J=12.0 and 5.6 Hz, 1H), 2.49 (dd, J=15.3 and 6.0 Hz, 1H), and 1.40 (s, 9H); $^{13}$C NMR (101 MHz, $CDCl_3$): δ 170.6, 163.8, 145.9, 137.4, 130.4, 110.9, 103.5, 80.9, 56.9, 53.71, 53.68, 53.4, 48.6, 43.8, and 28.0.

Method B: Reductive amination with sodium triacetoxyborohydride

To a solution of p-TSA salt 2-5 (100 g; 0.239 mmol) and glyoxal-1,1-dimethyl acetal (60 wt % in water; 39.3 mL; 0.261 mol) in THF (400 mL) was slowly added a suspension of sodium triacetoxyborohydride (79 g; 0.354 mol) in THF (200 mL) maintaining the batch temperature below 10° C. After the addition was complete, the suspension was rinsed with THF (40 mL) and added to the reaction mixture. The mixture was aged at 5–10° C. for 30 minutes and then at ambient temperature for 30 minutes. The mixture was cooled down to below 10° C. To the mixture was added aqueous sodium carbonate solution (1.2 L, 10 wt %), maintaining the batch temperature below 10° C. To the mixture was added EtOAc (750 mL). The organic layer was separated, washed with saturated aqueous sodium hydrogencarbonate (600 mL) and then water (500 mL). The organic layer was concentrated in vacuo and flushed with EtOAc to remove remaining water. The mixture was flushed with THF to remove residual EtOAc and the THF solution was used for the next reaction. The solution contained 74.1 g (92.2% yield) of the product 2-6.

Step K: Preparation of Compounds 3-1 and 3-2
Method A:

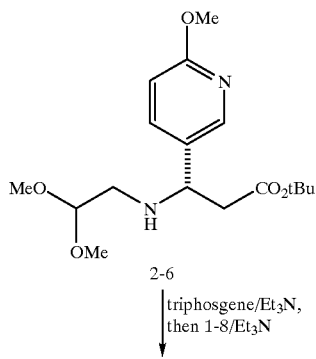

-continued

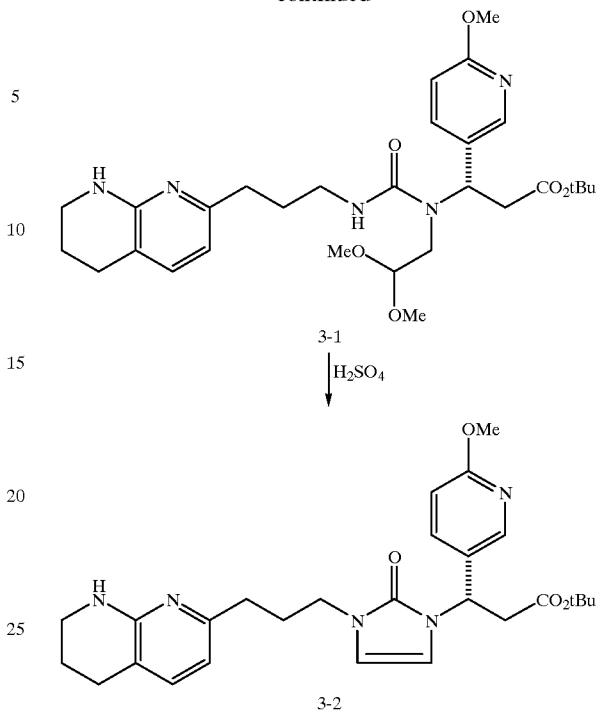

To a cold (−10° C.) solution of bis(trichloromethyl)carbonate (triphosgene) (3.0 g; 9.8 mmol) in anhydrous THF (60 mL) was slowly added a solution of acetal 2-6 (9.5 g; 85 wt %; 24 mmol) and triethylamine (4.4 mL; 32 mmol) in anhydrous TEF (35 mL), keeping the reaction temperature below 5° C. The reaction mixture was aged at 5° C. for 30 minutes and at ambient temperature for 30 minutes. The excess phosgene was purged from the reaction mixture with a helium sparge through a scrubber containing aqueous NaOH. To the mixture was added anhydrous THF (20 mL). To the resulting suspension was added amine 1-8 (5.3 g; 94 wt %; 26 mmol) and triethylamine (4.4 mL; 32 mmol) at 5° C. The suspension was stirred at 40° C. for 6 hours. The reaction mixture was cooled to ambient temperature and 2 M aqueous sulfuric acid (30 mL) was added to the mixture at 22° C. The mixture was stirred at ambient temperature for 10 hours. The reaction mixture was added to a mixture of iPAc (50 mL) and 2 M aqueous sulfuric acid (15 mL). The aqueous layer was separated and washed with iPAc (50 mL). To the aqueous layer was added iPAc (50 mL) and the pH of the aqueous layer was adjusted to 8.2 by addition of solid $Na_2CO_3$. The organic layer was separated, washed with dilute aqueous NaCl (33 mL) twice, and concentrated in vacuo to give crude 3-2 as an oil (24.7 g; 40.1 wt %; 85%). An authentic sample was purified by silica gel column chromatography as an oil.

$^1$H NMR (400 MHz; $CDCl_3$): δ 8.13 (d, J=2.8 Hz, 1H), 7.60 (dd, J=8.8 and 2.8 Hz, 1H), 7.04 (d, J=7.2 Hz, 1H), 6.70 (d, J=8.8 Hz, 1H), 6.34 (d, J=7.2 Hz, 1H), 6.32 (d, J=2.8 Hz, 1H), 6.18 (d, J=2.8 Hz, 1H), 5.59 (t, J=8.0 Hz, 1H), 4.81 (bs, 1H), 3.91 (s, 3H), 3.62 (m, 2H), 3.39 (m, 2H), 3.11 (dd, J=15.3 and 8.0 Hz, 1H), 2.97 (dd, J=15.3 and 8.0 Hz, 1H), 2.68 (t, J=6.4 Hz, 2H), 2.55 (t, J=7.6 Hz, 2H), 2.01 (m, 2H), 1.89 (m, 2H), and 1.35 (s, 9H); $^{13}$C NMR (101 MHz; $CDCl_3$) δ 168.8, 163.8, 156.7, 155.7, 152.4, 145.3, 137.9, 136.8, 127.8, 113.5, 111.4, 111.0, 110.9, 107.6, 81.4, 53.5, 51.5, 43.0, 41.6, 39.8, 34.5, 29.3, 27.9, 26.3, and 21.4.

Method B:

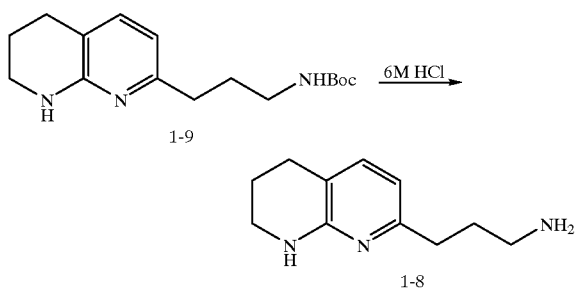

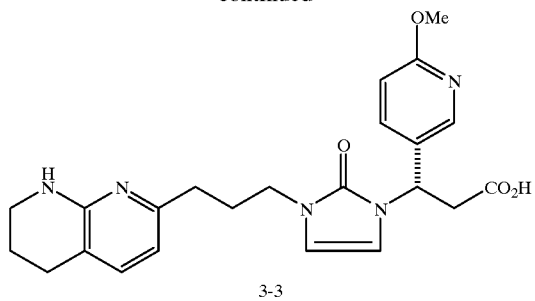

To compound 1-9 (for the preparation of 1-9, see U.S. Pat. No. 6,048,861) (10.4 g; 35 mmol) was added 6 M HCl (18 mL) under ice-cooling. The resulting solution was warmed to 35° C. for 1.5 hours. The pH of the solution was adjusted to about 7 with 50 wt % NaOH (~2 mL) at ambient temperature. After addition of 2-butanol (35 mL) to the mixture, the pH of the aqueous layer was further adjusted to about 11.5 with 50 wt % of NaOH (~2 mL). The organic layer was separated, washed with saturated aqueous NaCl (10 mL), and dried by distillation at constant volume to remove water to yield a solution of 1-8 in 2-butanol.

A solution of 2-6 (10.0 g; 29 mmol) and triethylamine (5.5 mL; 40 mmol) in THF (45 mL) was added to a solution of bis(trichloromethyl)carbonate (3.51 g; 12 mmol) and THF (75 mL) below 0° C. over 30 minutes. The mixture was aged for 2 hours at ambient temperature. To the mixture was added the 2-butanol solution of 1-8, prepared above, and triethylamine (5.5 mL; 40 mmol). The mixture was aged at 45° C. for 3 hours. To the mixture was added water (20 mL). The organic layer was separated. To the organic layer was added 2 M sulfuric acid (40 mL) and the mixture was aged for 18 hours at ambient temperature. To the mixture was added iPAc (50 mL) and the organic layer was separated. The organic layer was extracted with 2M sulfuric acid (20 mL). The combined aqueous layers were washed with iPAc (50 mL). To a mixture of the resulting aqueous layer and iPAc (80 mL) was added aqueous sodium hydroxide (5 N; 40 mL) under an ice bath to adjust the pH of the aqueous layer to about 8.3. The organic layer was separated and washed with water (3×45 mL). The solution containing the crude 3-2 (12.0 g; 84%) in iPAc was used in the next step without further purification.

Step L: Preparation of Compound 3-3

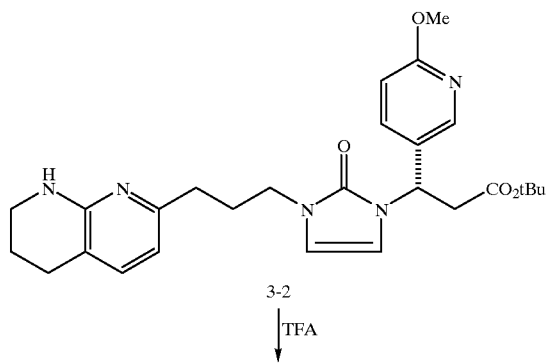

Method A:

To a solution of the t-butyl ester (3-2; 37.1 wt % in iPAc; 50 g; 18.6 g as corrected; 0.101 mol) and anisole (21.9 g) was slowly added trifluoroacetic acid (462 g) at 2–3° C. The resulting mixture was stirred at room temperature until reaction completion (4.5 h). Trifluoroacetic acid was removed under vacuum. Isopropyl acetate (100 mL) was added and the solvents removed under vacuum. The flask was cooled with ice and 170 mL of iPAc was added followed by the slow addition of saturated aqueous $NH_4OH$ (170 mL) until pH=10.4. The aqueous layer was separated, washed with 300 mL of iPAc, and concentrated under vacuum until pH=6.5. The resulting solution was subjected to a resin column (Amberchrome CG-161C, Toso-Haas) and first eluted with water to remove trifluoroacetic acid. Subsequently, 50% acetone/water was used to elute the desired product. The fractions containing the product were combined, concentrated in vacuo, and aged at 5° C. The resulting solids were filtered and washed with cold water to give 37.5 g of carboxylic acid 3-3 (85%). Compound 3-3 can be recrystallized from aqueous alcohols, such as methanol, ethanol, or isopropanol, or aqueous acetone.

$^1$H NMR (400 MHz; $CD_3OD$): δ 8.16 (d, J=2.6 Hz, 1H), 7.73 (dd, J=8.6 and 2.6 Hz, 1H), 7.45 (d, J=7.4 Hz, 1H), 6.81 (d, J=8.6 Hz, 1H), 6.54 (d, J=3.1 Hz, 1H), 6.53 (d, J=7.4 Hz, 1H), 6.50 (d, J=3.1 Hz, 1H), 5.70 (dd, J=11.6 and 4.2 Hz, 1H), 3.90 (s, 3H), 3.76 (ddd, J=14.1, 9.7 and 4.2 Hz, 1H), 3.51 (dt, J=14.1 and 5.0 Hz, 1H), 3.46 (m, 2H), 2.99 (dd, J=14.0 and 11.6 Hz, 1H), 2.85 (dd, J=14.0 and 4.2 Hz, 1H), 2.77 (t, J=6.4 Hz, 2H), 2.70 (ddd, J=13.8, 8.2 and 6.0 Hz, 1H), 2.50 (dt, J=13.8 and 8.0 Hz, 1H), and 2.16–1.85 (m, 4H); $^{13}$C NMR (101 MHz, $CD_3OD$): δ 177.6, 163.9, 153.8, 152.2, 148.8, 145.0, 140.1, 137.9, 128.6, 118.2, 111.1, 110.4, 109.5, 108.6, 52.7, 52.1, 41.5, 40.8, 40.3, 28.9, 28.1, 25.1, and 19.4.

Method B:

To a solution of 3-2 (140 mg/mL; 220 mL; 30.8 g; 62.4 mmol) in iPAc was added aqueous sulfuric acid (3.06 M; 150 mL), maintaining the batch temperature below 10° C. The aqueous layer was separated and aged at 40° C. for 3 hours. The solution was cooled to 10° C. The pH of the solution was adjusted to about 2 with 50 wt % sodium hydroxide and added SP207 resin (310 mL). The pH of the resulting suspension was adjusted to about 5.9 with 50 wt % sodium hydroxide, and the resulting suspension was aged at ambient temperature for 4 hours. The suspension was filtered and the resin was washed with 930 mL of water. The resin was washed with 70% of acetone-water (v/v; 1.5 L). The fractions containing the product were combined and concentrated to remove acetone. The resulting suspension was cooled to 5° C. The product was collected by filtration and washed with 20 mL of cold water. The crystals were dried at 30° C. under vacuum to give 3-3 (23.5g; 86% yield).

Method C:

A solution of 3-2 in iPAc (9.5 g 19.2 mmol; 110 mL) was extracted with aqueous sulfuric acid (3M; 47.5 mL). The aqueous layer was separated and stirred at 40° C. for 3 hours under nitrogen until hydrolysis was completed. The mixture was cooled to about 5° C. and the pH was adjusted to about 1 with aqueous sodium hydroxide (50 wt %). To the mixture was added methanol (71.3 mL). The pH was further adjusted to about 5.0 with aqueous sodium hydroxide (50 wt %) and additional methanol (71.3 mL) was added. The pH was finally adjusted to about 5.9 with aqueous sodium hydroxide (50 wt %). The suspension was stirred at ambient temperature for 1 hour and the resulting salt was filtered and washed with methanol (2×20 mL). The combined filtrate and washings were concentrated and flushed with isopropanol to remove methanol and water. The resulting suspension was stirred at 60° C. to obtain a homogeneous solution. The solution was slowly cooled to 5° C. The suspension was filtered, washed with cold isopropanol (20 mL), and dried under reduced pressure to give colorless crystalline 3-3 (8.1 g; 94 wt %; 91%).

Step M: Preparation of Compound 3-4

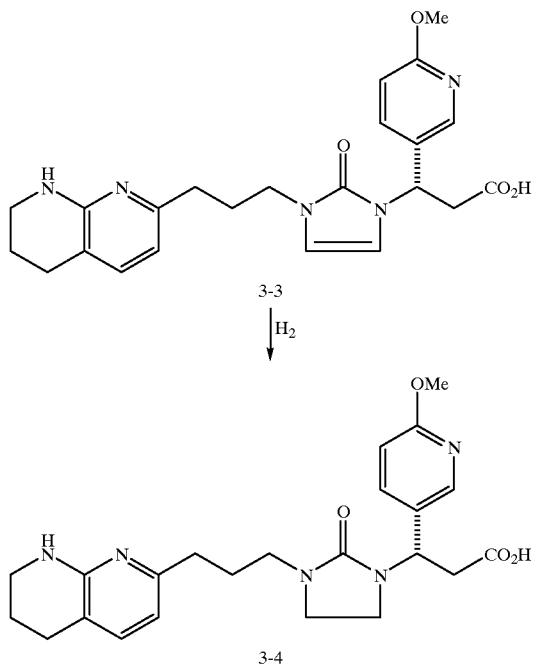

A suspension of 3-3 (105 g), water (247 mL), 5 M NAOH (84 mL) and 20% Pd(OH)$_2$/C (21 g) was hydrogenated at 120 psi H$_2$ and 80° C. for 18 h. The pH was adjusted to 9.0 by addition of concentrated HCl (18 mL). The solids were removed by filtration through a pad of Solka Flok (13 g) and the pad was rinsed with 200 mL of water. The pH of the aqueous solution was adjusted to 6.4 by addition of concentrated HCl and the solution was seeded and aged at 0° C. for 1 h. The solids were collected by filtration and dried under dry nitrogen at room temperature for up to 24 hours to provide 84.5 g (80%) of 3-4 as a colorless crystalline solid. 3-4 is a highly crystalline compound, formed by the process of the present invention in >99.5% enantiomeric excess and >99.5% chemical purity as determined by high-performance liquid chromatography. The 300 MHz NMR spectrum in CD$_3$OD was identical to that disclosed in U.S. Pat. No. 6,017,926.

The crystalline form obtained was characterized by a differential scanning calorimetry curve, at a heating rate of 10° C. /min. under nitrogen, exhibiting a minor endotherm with a peak temperature of about 61° C. due to solvent loss and a major melting endotherm with a peak temperature of about 122° C. (extrapolated onset temperature of about 110° C.). The X-ray powder diffraction showed absorption bands at spectral d-spacings of 3.5, 3.7, 4.3, 5.0, 5.7, 7.1, and 7.5 angstroms. The FT-IR spectrum (in KBr) showed absorption bands at 2922, 2854, 1691, 1495, 1460, 1377, 1288, 1264, and 723 cm$^{-1}$.

The content of water as obtained with Karl-Fischer titration was 1.7 wt % (the theory for a hemihydrate is 2.0%).

Alternative Route to 3-4 from 3-2:

Step A: Preparation of Compound 3-5

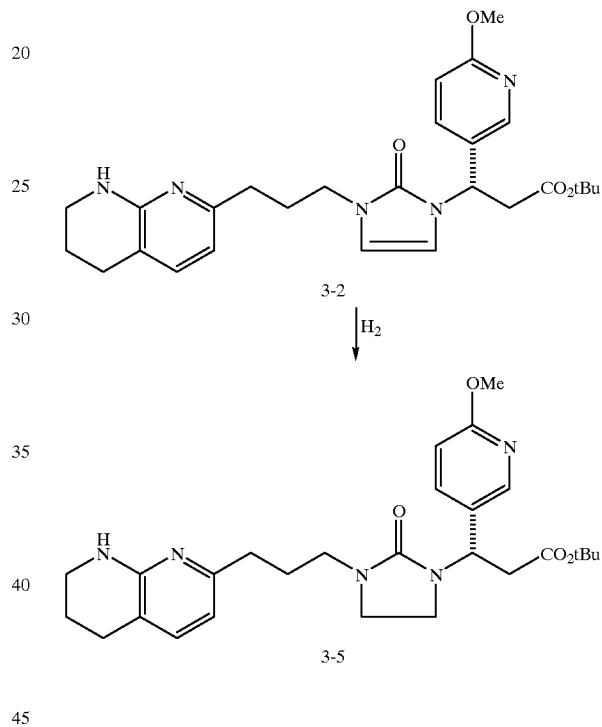

A solution of 3-2 (3.40 g) in methanol (40 mL) was hydrogenated under 40 psi of hydrogen in the presence of Pd(OH)$_2$ (1.36 g) at 40° C. for 3 days. The catalyst was filtered through a pad of Solka Flok and rinsed with MeOH (5 mL). The filtrate and washings were combined and concentrated. The residue was purified by silica gel column chromatography eluted with a mixture of EtOAc, EtOH, conc. NH$_4$OH, and water (100:0:0:0 to 95:4.2:0.4:0.4). The fractions containing the product were combined and concentrated in vacuo to give 3-5 (2.20 g) as an oil.

$^1$H NMR (250 MHz; CDCl$_3$): δ 8.06 (d, J=2.5 Hz, 1H), 7.57 (dd, J=8.6 and 2.5 Hz; 1H), 7.01 (d, J=7.3 Hz, 1H), 6.70 (d, J=8.6 Hz, 1H), 6.33 (d, J=7.3 Hz, 1H), (t, J=8.2 Hz, 1H), 4.76 (broad s, 1H), 3.91 (s, 3H), 3.40–3.33 (m, 2H), 3.33–3.14 (m, 5H), 2.97–2.82 (m, 3H), 2.66 (t, J=6.3 Hz, 2H), 2.51 (t, J=7.7 Hz, 2H), 1.93–1.76 (m, 4H), and 1.36 (s, 9H). $^{13}$° C. NMR (63.9 MHz, CDCl$_3$): δ 169.5, 163.5, 159.9, 156.5, 155.3, 145.2, 138.3, 136.8, 126.9, 113.5, 111.1, 110.7, 80.9, 53.3, 50.5, 43.7, 42.5, 41.4, 38.2, 37.5, 34.5, 27.7, 27.4, 26.1, and 21.2.

Step B: Preparation of Compound 3-4

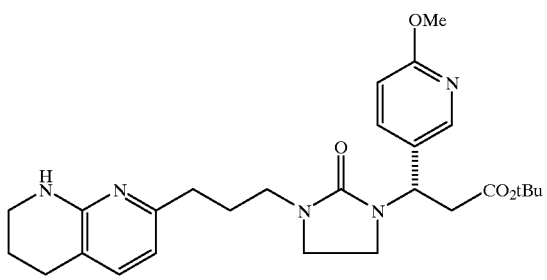

To a solution of 3-5 (418 mg) and anisole (0.42 mL) in dichloromethane (1.26 mL) was added TFA (0.84 mL) at ambient temperature. After stirring overnight, additional TFA (0.4 mL) was added and the mixture was stirred for additional 4 hours. The mixture was concentrated in vacuo. The residue was purified by silica gel column chromatography eluted by a mixture of EtOAc:EtOH: conc. ammonium hydroxide:water (95:4.2:0.4:0.4 to 50:42:4:4). The fractions containing the product were collected and concentrated in vacuo to give 3-4 (290 mg).

What is claimed is:

1. A process of preparing a compound of stuctural formula (II):

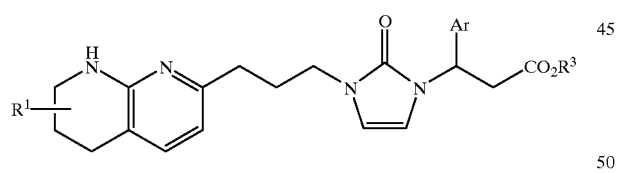

wherein
Ar is mono-or di-substituted phenyl, naphthyl, pyridyl, furyl, thienyl, pyrrolyl, oxazolyl, thiazolyl, isoxazolyl, isothiazolyl, imidazolyl, tetrazolyl, pyrazolyl, pyrimidyl, pyrazinyl, quinolyl, isoquinolyl, benzofuryl, benzothienyl, benzimidazolyl, benzthiazolyl, benzoxazolyl, indolyl, isoindolyl, purinyl, or carbazolyl, wherein the substituent is independently selected from the group consisting of hydrogen, $C_{1-6}$ alkyl, halogen, $C_{3-6}$ cycloalkyl, $C_{1-3}$ acylamino, $C_{1-4}$ alkoxy, $C_{1-5}$ alkoxycarbonyl, cyano, trifluoromethyl, trifluoromethoxy, hydroxy, amino, $C_{1-4}$ alkylamino, di-$C_{1-4}$ alkylamino, and $C_{1-5}$ alkylcarbonyloxy;
$R^1$ is selected from the group consisting of hydrogen, halogen, $C_{1-10}$ alkyl, $C_{3-6}$ cycloalkyl, and $C_{1-3}$ alkoxy; and $R^3$ is $C_{1-4}$ alkyl, phenyl-$C_{1-3}$ alkyl, diphenylmethyl, or triphenylmethyl;

comprising the step of treating an amine of structural formula (III):

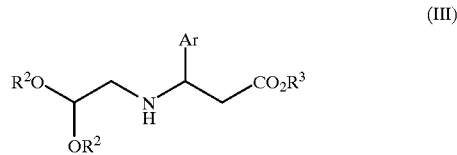

wherein $R^2$ is $C_{1-4}$ alkyl;
with an amine of structural formula (IV):

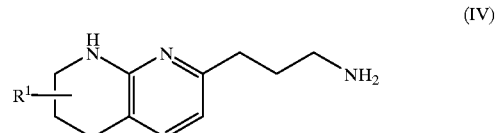

in the presence of phosgene or a phosgene equivalent and base to produce a compound of structural formula (VI):

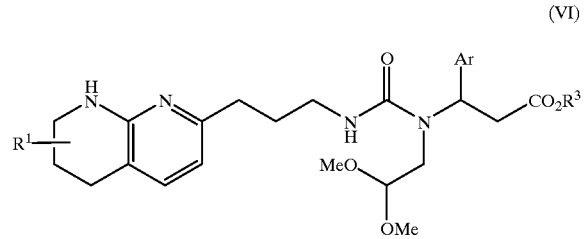

followed by treatment with aqueous acid.

2. The process of claim 1 additionally comprising the step of producing a compound of structural formula (III):

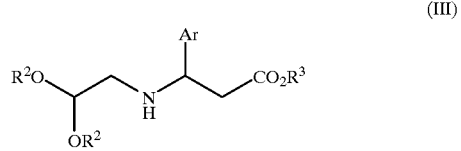

by treating a compound of structural formula (V):

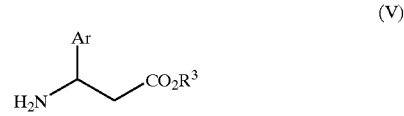

with glyoxal-1,1-di-$C_{1-4}$ alkyl acetal in the presence of a reducing agent.

3. The process of claim 1 wherein $R^1$ is hydrogen and Ar is 6-methoxy-pyridin-3-yl.

4. The process of claim 3 wherein Ar is (S)-(6-methoxy-pyridin-3-yl).

5. The process of claim 4 wherein $R^3$ is t-butyl.

6. A compound selected from

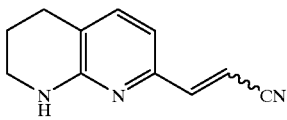 and

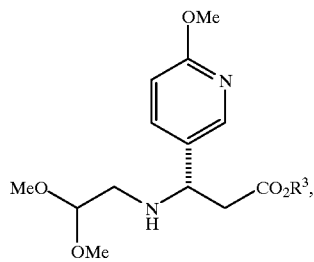

wherein $R^3$ is $C_{1-4}$ alkyl, phenyl-$C_{1-3}$ alkyl, diphenylmethyl, or triphenylmethyl.

7. The process of claim 1 wherein the phosgene equivalent is bis(trichloromethyl) carbonate (triphosgene).

8. The process of claim 2 wherein the reducing agent is sodium cyanoborohydride or sodim triacetoxyborohydride.

9. The process of claim 1 wherein the aqueous acid is aqueous sulfuric acid.

10. A process for preparing a compound of structural formula (I):

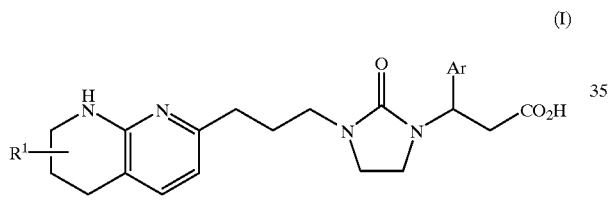

(I)

wherein

Ar is mono-or di-substituted phenyl, naphthyl, pyridyl, furyl, thienyl, pyrrolyl, oxazolyl, thiazolyl, isoxazolyl, isothiazolyl, imidazolyl, tetrazolyl, pyrazolyl, pyrimidyl, pyrazinyl, quinolyl, isoquinolyl, benzofuryl, benzothienyl, benzimidazolyl, benzthiazolyl, benzoxazolyl, indolyl, isoindolyl, purinyl, or carbazolyl, wherein the substituent is independently selected from the group consisting of hydrogen, $C_{1-6}$ alkyl, halogen, $C_{3-6}$ cycloalkyl, $C_{1-3}$ acylamino, $C_{1-4}$ alkoxy, $C_{1-5}$ alkoxycarbonyl, cyano, trifluoromethyl, trifluoromethoxy, hydroxy, amino, $C_{1-4}$ alkylamino, di-$C_{1-4}$ alkylamino, and $C_{1-5}$ alkylcarbonyloxy, and $R^1$ is selected from the group consisting of hydrogen, halogen, $C_{1-10}$ alkyl, $C_{3-6}$ cycloalkyl, and $C_{1-3}$ alkoxy;

comprising the steps of:

(a) producing a compound of structural formula (III):

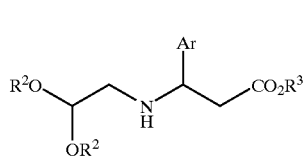

(III)

wherein $R^3$ is $C_{1-4}$ alkyl or phenyl-$C_{1-3}$ alkyl;

by treating a compound of structural formula (V):

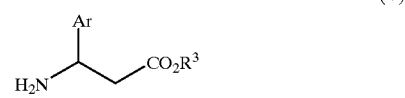

(V)

with glyoxal-1,1-di-$C_{1-4}$ alkyl acetal in the presence of a reducing agent, and isolating the resulting product;

(b) preparing a compound of structural formula (II):

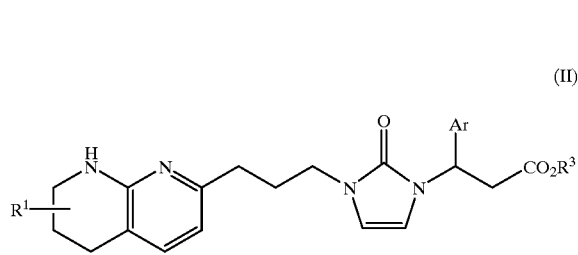

(II)

by treating an amine of structural formula (III):

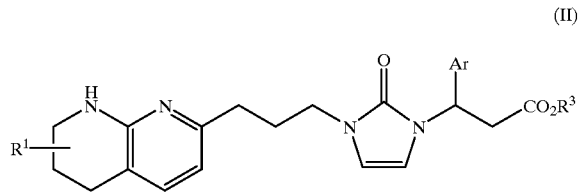

(III)

wherein $R^2$ is $C_{1-4}$ alkyl and $R^3$ is $C_{1-4}$ alkyl or phenyl-$C_{1-3}$ alkyl, with an amine of structural formula (IV):

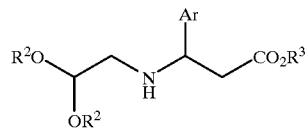

(IV)

wherein $R^1$ is as defined above, in the presence of phosgene or a phosgene equivalent and base to produce a compound of structural formula (VI):

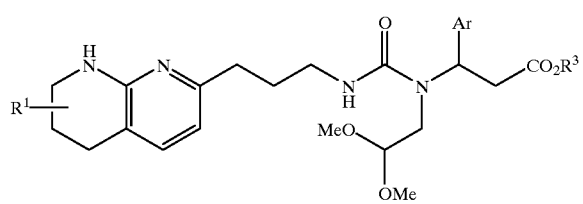

(VI)

followed by treatment with aqueous acid;

(c) cleaving the $R^3$ protecting group and (d) reducing the imidazolin-2-one double bond in a compound of structural formula (II); and

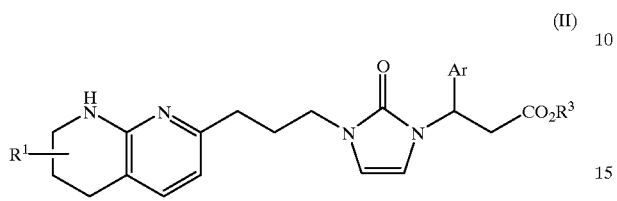
(II)

(e) isolating the resulting product.

11. The process of claim 2 wherein glyoxal-1,1-di-$C_{1-4}$ alkyl acetal is glyoxal-1,1-dimethyl acetal.

12. The process of claim 10 wherein said step (d) of reducing the imidazolin-2-one double bond is carried out before said step (c) of cleaving the $R^3$ protecting group.

13. A crystalline compound which is

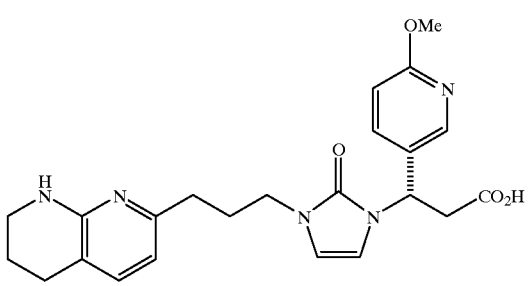

characterized by characteristic absorption bands obtained from X-ray powder diffraction pattern I at spectral d-spacings of 3.4, 3.5, 4.9, 5.3, 6.2 and 8.1; pattern II at spectral d-spacings of 3.5, 3.6, 4.8, 5.5, 6.0, and 8.3 angstroms; pattern m at spectral d-spacings of 3.4, 3.5, 3.6, 3.8, 4.1, 5.0 and 15.7 angstroms; pattern IV at spectral d-spacings of 3.5, 3.8–3.9, 4.4, 4.5–4.6, 6.4, 12.6, and 18.9–19.0 angstroms; pattern V at spectral d-spacings of 3.5, 3.8–3.5, 3.9, 4.4, 4.5–4.6, 6.4, 13.0, and 18.9–19.0 angstroms; or pattern VI at spectral d-spacings of 3.5, 3.8–3.9, 4.4, 4.5–4.6, 6.4, 15.7, and 18.9–19.0 angstroms.

* * * * *